(12) United States Patent
Mellett et al.

(10) Patent No.: US 11,650,672 B2
(45) Date of Patent: May 16, 2023

(54) HEALTHCARE INFORMATION MANIPULATION AND VISUALIZATION CONTROLLERS

(71) Applicant: HOLOGIC, INC., Marlborough, MA (US)

(72) Inventors: Alyssa Mellett, Kennesaw, GA (US); Russell Kroll, Atlanta, GA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/464,000

(22) PCT Filed: Nov. 22, 2017

(86) PCT No.: PCT/US2017/063079
§ 371 (c)(1),
(2) Date: May 24, 2019

(87) PCT Pub. No.: WO2018/098329
PCT Pub. Date: May 31, 2018

(65) Prior Publication Data
US 2020/0363877 A1    Nov. 19, 2020

Related U.S. Application Data

(60) Provisional application No. 62/426,398, filed on Nov. 25, 2016.

(51) Int. Cl.
*G06F 3/023* (2006.01)
*G16H 40/20* (2018.01)
(Continued)

(52) U.S. Cl.
CPC ........... *G06F 3/0238* (2013.01); *G05B 15/02* (2013.01); *G06F 3/0312* (2013.01);
(Continued)

(58) Field of Classification Search
CPC ...... G06F 3/0238; G16H 40/20; G16H 40/63; G16H 50/20; G16H 30/20; G16H 30/40; G05B 15/02
See application file for complete search history.

(56) References Cited

U.S. PATENT DOCUMENTS 5,404,152 A * 4/1995 Nagai ................... G06F 3/0362
345/157
6,525,713 B1 * 2/2003 Soeta ................... G06F 3/0312
345/159
(Continued)

FOREIGN PATENT DOCUMENTS

EP      1004957 A1    5/2000
EP      2783632 A1    10/2014
(Continued)

OTHER PUBLICATIONS

International Search Report and Written Opinion for application PCT/US2017/063079, dated Mar. 9, 2018, 10 pages.
(Continued)

*Primary Examiner* — David Tung
(74) *Attorney, Agent, or Firm* — Merchant & Gould P.C.

(57) ABSTRACT

Methods and apparatus are disclosed for viewing and manipulating digital images. One example apparatus includes a controller configured to receive user input via a plurality of context-adaptive button controls, each of the plurality of context-adaptive button controls being associated with at least one function for viewing and manipulating digital images. The controller configured to determine at least one context of the digital medical images and change the at least one function for viewing and manipulating digital images based on the determined context.

19 Claims, 48 Drawing Sheets

(51) Int. Cl.
*G16H 30/20* (2018.01)
*G16H 50/20* (2018.01)
*G16H 30/40* (2018.01)
*G16H 40/63* (2018.01)
*G05B 15/02* (2006.01)
*G06F 3/03* (2006.01)
*G06F 3/0485* (2022.01)

(52) U.S. Cl.
CPC ........... *G06F 3/0485* (2013.01); *G16H 30/20* (2018.01); *G16H 30/40* (2018.01); *G16H 40/20* (2018.01); *G16H 40/63* (2018.01); *G16H 50/20* (2018.01)

(56) References Cited

U.S. PATENT DOCUMENTS

| | | | | |
|---|---|---|---|---|
| 8,239,784 | B2* | 8/2012 | Hotelling | G06F 3/0418 715/830 |
| 2005/0140656 | A1* | 6/2005 | McLoone | G06F 3/0219 345/168 |
| 2008/0130979 | A1* | 6/2008 | Ren | G06K 9/6201 382/132 |
| 2008/0267467 | A1 | 10/2008 | Sokulin et al. | |
| 2009/0033522 | A1* | 2/2009 | Skillman | G06F 1/1692 341/23 |
| 2009/0174663 | A1* | 7/2009 | Rudd | G06F 3/04886 345/173 |
| 2010/0194682 | A1* | 8/2010 | Orr | G06F 3/04886 345/156 |
| 2010/0325088 | A1 | 12/2010 | Hsieh et al. | |
| 2011/0270358 | A1* | 11/2011 | Davis | A61N 1/36185 607/60 |
| 2011/0314405 | A1* | 12/2011 | Turner | G06F 3/0238 715/773 |
| 2012/0133600 | A1* | 5/2012 | Marshall | G06F 3/0416 345/173 |
| 2012/0154431 | A1* | 6/2012 | Fram | G06F 3/038 345/619 |
| 2014/0013280 | A1 | 1/2014 | Yoshioka et al. | |
| 2014/0123183 | A1 | 5/2014 | Fujimoto | |
| 2015/0094581 | A1 | 4/2015 | Butler | |
| 2016/0162163 | A1 | 6/2016 | Park et al. | |

FOREIGN PATENT DOCUMENTS

| | | |
|---|---|---|
| EP | 2913769 A1 | 9/2015 |
| EP | 2952376 A2 | 12/2015 |
| JP | 2000-322198 | 11/2000 |
| JP | 2004-038947 | 2/2004 |
| JP | 2004-357789 | 12/2004 |
| JP | 2008-199293 | 8/2008 |

OTHER PUBLICATIONS

European Communication in Application 17817460.3, dated Mar. 25, 2020, 7 pages.
European Summons to Attend Oral Proceedings in Application 17817460.3, mailed Oct. 21, 2020, 9 pages.
PCT International Preliminary Report on Patentability in Application PCT/US2017/063079, dated Jun. 6, 2019, 8 pages.

* cited by examiner

| | 410 | | | 405 |
|---|---|---|---|---|
| | MENU ✕ | | | 12.01.2016<br>3:18 PM |
| | PATIENT LIST | NAME | PATIENT ID | DATE OF BIRTH |
| | LAST PATIENT | PATIENT NAME | XXXXXXXXXX | XX-XX-XXXX |
| | DAILY REPORT | PATIENT NAME | XXXXXXXXXX | XX-XX-XXXX |
| | SETTINGS | PATIENT NAME | XXXXXXXXXX | XX-XX-XXXX |
| | | PATIENT NAME | XXXXXXXXXX | XX-XX-XXXX |
| | | PATIENT NAME | XXXXXXXXXX | XX-XX-XXXX |
| | SIGN OUT | PATIENT NAME | XXXXXXXXXX | XX-XX-XXXX |

USER ID

PASSWORD

LOGIN

TOUCH AND HOLD IDENTIFICATION FINGER ANYWHERE

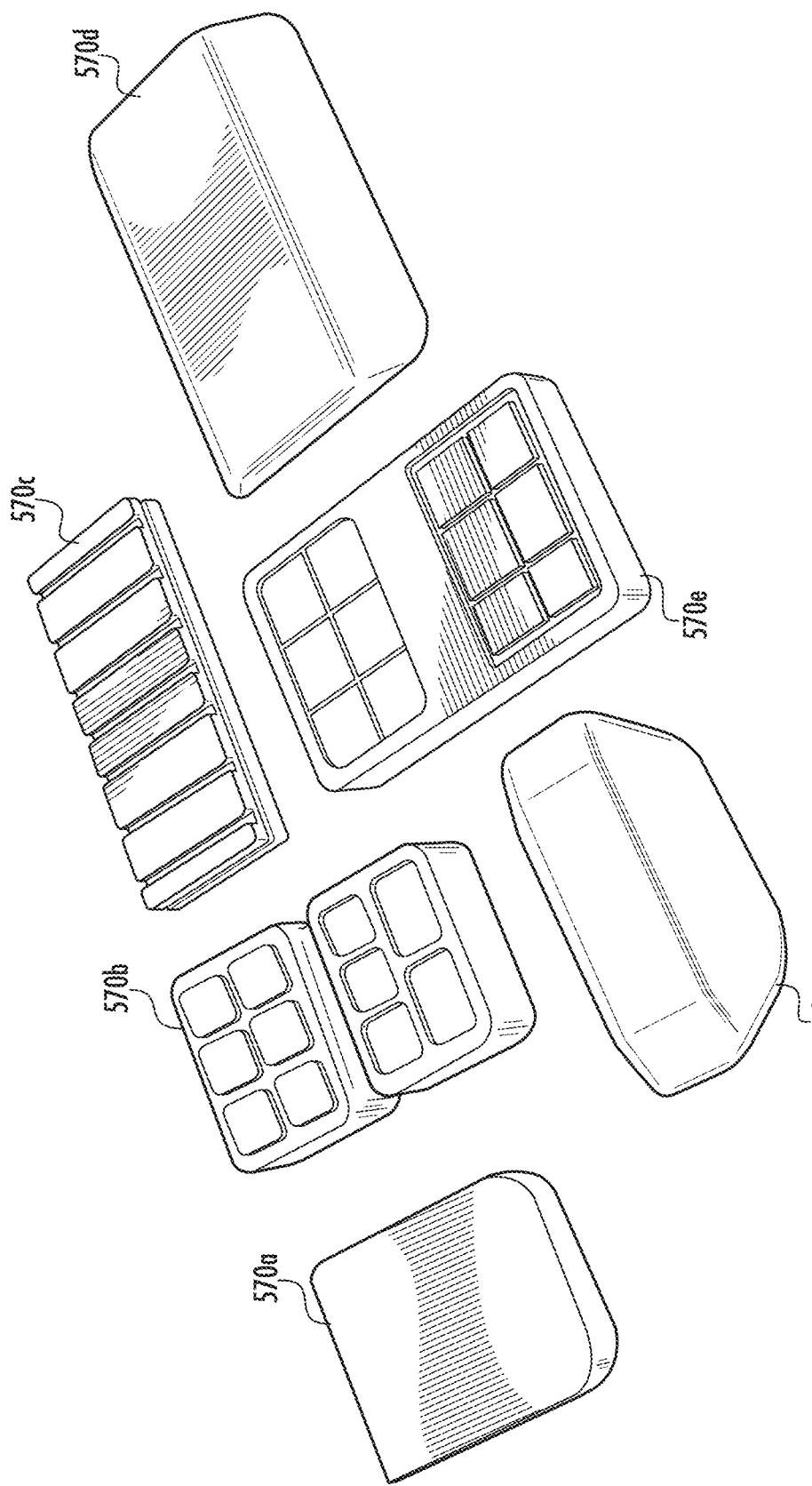

HEALTHCARE INFORMATION MANIPULATION AND VISUALIZATION CONTROLLERS

CROSS-REFERENCE TO RELATED APPLICATIONS

This application is a U.S. National Phase of International Patent Application No. PCT/US2017/063079, filed Nov. 22, 2017, which claims the benefit of U.S. Provisional Application No. 62/426,398, filed Nov. 25, 2016. The contents of both International Patent Application No. PCT/US2017/063079 and U.S. Provisional Patent Application No. 62/426,398 are hereby incorporated herein by reference in their respective entireties for all purposes.

FIELD OF THE DISCLOSURE

The disclosure generally relates to healthcare information systems, and more particularly to controllers for manipulating, comparing, and/or visualizing information accessible through healthcare information systems.

BACKGROUND OF THE INVENTION

Healthcare professionals such as radiologists interact with various forms of healthcare information during patient diagnosis and treatment processes. For example, during a healthcare workflow, a radiologist may access patient healthcare information stored in one or more centralized information systems from a workstation. The healthcare information may include patient records and diagnostic images for multiple modalities, such as ultrasound, x-ray, magnetic resonance (MR or MRI), and/or computed tomography (CT). Each type of healthcare information requires particular functions for efficient manipulation and visualization, such as scrolling through a patient medical history, reading or navigating through a "stack" or series of medical images, and annotating patient records. However, conventional workstation controllers for accessing healthcare information generally include a restricted function set that is focused on a particular imaging modality or type of healthcare information. Accordingly, the efficiency and effectiveness of the overall workflow for a healthcare professional over different phases of treatment and various forms of healthcare information is currently limited.

It is appreciated that radiologists work space and environment is unique than those of other health professionals. Radiologists are very sensitive to and aware of their reading environments which are dark, quiet, and highly controlled spaces. Over the years they have developed particular workflows and methods that they use to view images or even image reading postures. It is important for the radiologists to be extremely focused on the diagnostic and screening images to prevent errors and ensure accuracy. This is because any error or inaccuracy could be a false positive detection of cancer, or a missed diagnosis. Typically radiologists view thousands of images each day, spending their whole day in front of an image viewing workstation. In addition, radiologists need to be extremely efficient as they typically spend about 30 seconds to review a patient's images and 90 seconds reporting the outcome of that review. Time spend managing the workstation or it's controls to get to right menu or the right key is time spent inefficiently resulting in longer review times, the need to hire more radiologists, and for the patient, longer wait times to get their results or longer wait times to get an appointment. Every time a radiologist has to look away from the display screen while reviewing an image, it is a distraction, and can mean an error in diagnosing cancer. A typical radiologist has up to three and sometimes four monitors they use to view images. While having multiple displays is desired, space in radiology suites is at a premium. In themselves, the displays are large and expensive allowing for images to be viewed in high resolution.

It is with respect to these and other considerations that the present inventions may be useful.

BRIEF DESCRIPTION OF THE DRAWINGS

By way of example, a specific embodiment of the disclosed device will now be described, with reference to the accompanying drawings, in which:

FIGS. 2A-2K depict various aspects of a healthcare information controller according to a first embodiment.

FIGS. 4A-4D depict controller display screens according to some embodiments.

FIGS. 5A-5K depict various aspects of a controller according to a third embodiment.

DETAILED DESCRIPTION

Figure 1:
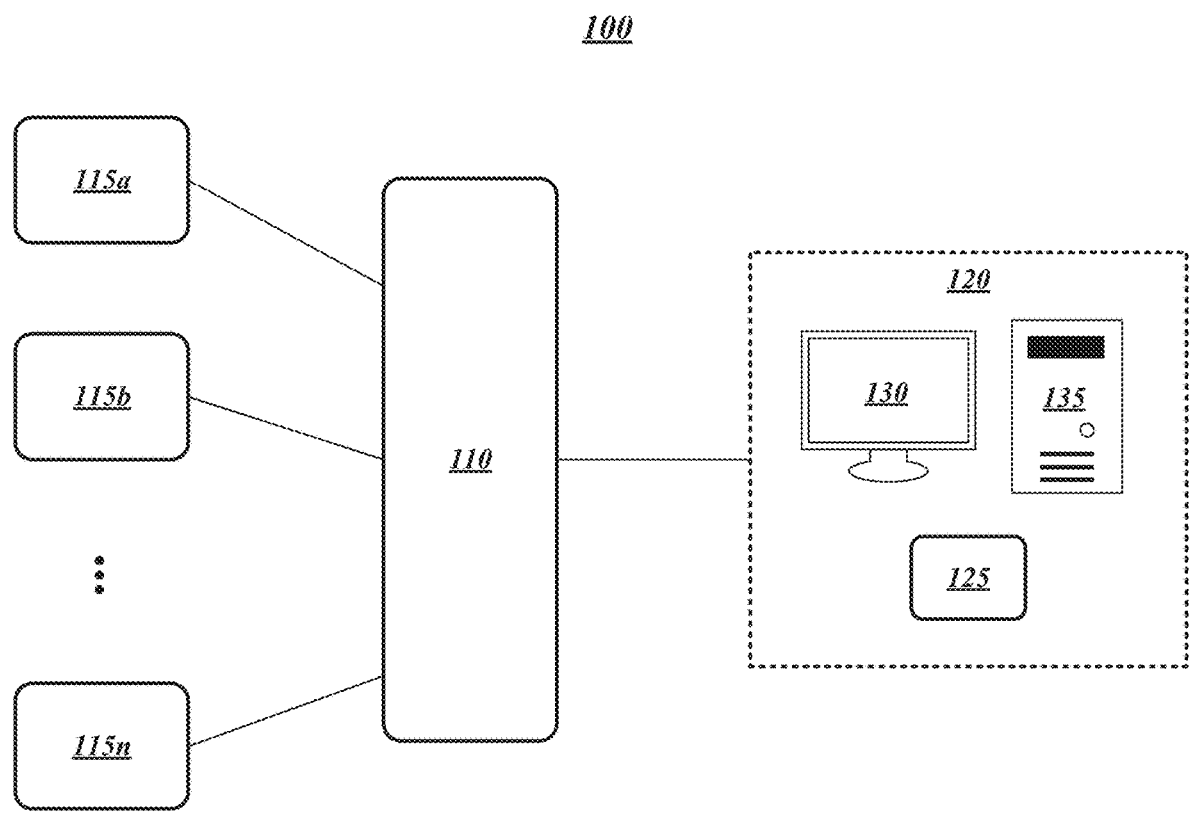
FIG. 1 illustrates an example of an operating environment 100 that may be representative of various embodiments.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

The workstation controller described herein according to various embodiments, solves the problems described above by providing a controller that is ergonomic, easy to use and keeps the radiologist within the reading zone. The controller uses a minimalist design that allows the radiologist to use the functions associated with the controller without having to look down to see the function being accessed. The controller further minimizes the amount of desk space used in the radiologist's suite by keeping the most frequently used functions within reach while allowing the less frequently used functions to still be accessible. The controller increases efficiency for the radiologist by keeping everything within easy reach and minimizes the amount of time spend on "housekeeping" such as looking for additional images, functions, or clicking through numerous menus. FIG. 1 illustrates an example of an operating environment 100 that may be representative of various embodiments. The operating environment 100 depicted in FIG. 1 may include one or more healthcare information sources 115a-n configured to provide healthcare information to a healthcare information system 110. In some embodiments, a healthcare information source 115a-n may include a computing device, medical imaging device, healthcare monitor, and/or the like configured to generate healthcare information. Non-limiting examples of healthcare information sources 115a-n may include a mammogram acquisition device, a breast tomosynthesis device, an x-ray imaging device, a fluoroscopy imaging device, an ultrasound (US) imaging device, a computed tomography (CT) imaging device, a magnetic resonance imaging (MR or MRI) device, a positron emission tomography (PET) imaging device, and/or the like. The healthcare information system 110 may include various information systems capable of storing and providing access to healthcare information, including, without limitation, a hospital information system (HIS), a radiology information system (RIS), a picture archiving and communication system (PACS), and/or the like. Healthcare information may include any type of information used by a healthcare professional for diagnosing, treating, or otherwise interacting with medical information of a patient. Non-limiting examples of healthcare information may include digital patient records, digital medical images, and/or the like.

As shown in FIG. 1, a workstation 120 may be used to access healthcare information through the healthcare information system 110. The workstation 120 may include a healthcare information controller ("controller") 125 configured to receive user input for interacting with the healthcare information presented via a monitor 130 of the workstation 120. Interacting with healthcare information may generally include visualizing or viewing (e.g., viewing a medical image or patient record presented via a display), reading, scrolling (e.g., scrolling through a series of medical images presented via a display), manipulating, editing, annotating, downloading, navigating, comparing, or otherwise interfacing with healthcare information presented by workstation computing device 135 via monitor 130.

The controller 125 may be configured to provide control signals to a workstation computing device 135 executing a healthcare information software application operative to access and present healthcare information. For example, the healthcare information software application may be capable of processing and displaying DICOM medical images, such as mammography and/or breast tomosynthesis ("TOMO") images. In some embodiments, the healthcare information software application may provide various image processing and measurement tools to facilitate visualization, manipulation, navigation, comparison, and/or interpretation of medical images. Controller 125 may be configured to support interaction with healthcare information presented by multi-modality workstation computing devices 135 and/or healthcare information software applications operative on a workstation computing device 135. In addition, controller 125 may operate to integrate and/or incorporate interaction with various types of healthcare information beyond information specific to medical images including, without limitation, digital patient records, word processing documents, spreadsheet documents, portable document format (PDF) documents, databases, image files, video files, audio files, and/or the like.

In some embodiments, controller 125 may include logic, implemented in hardware and/or software elements, configured to control aspects of the operation of controller 125. For example, controller 125 may execute a controller software application configured to control the functionality of controller components, such as buttons, navigation elements (e.g., scroll wheels), touch screen elements, and/or display screens. In some embodiments, workstation computing device 135 may include logic, implemented in hardware and/or software elements (e.g., a healthcare information software application), configured to control aspects of the operation of controller 125 according to some embodiments. The functionality of a controller 125 configured according to some embodiments may be controlled via logic of the controller 125, logic of the workstation computing device 135, and/or some combination thereof. Embodiments are not limited in this context.

Figure 2A:
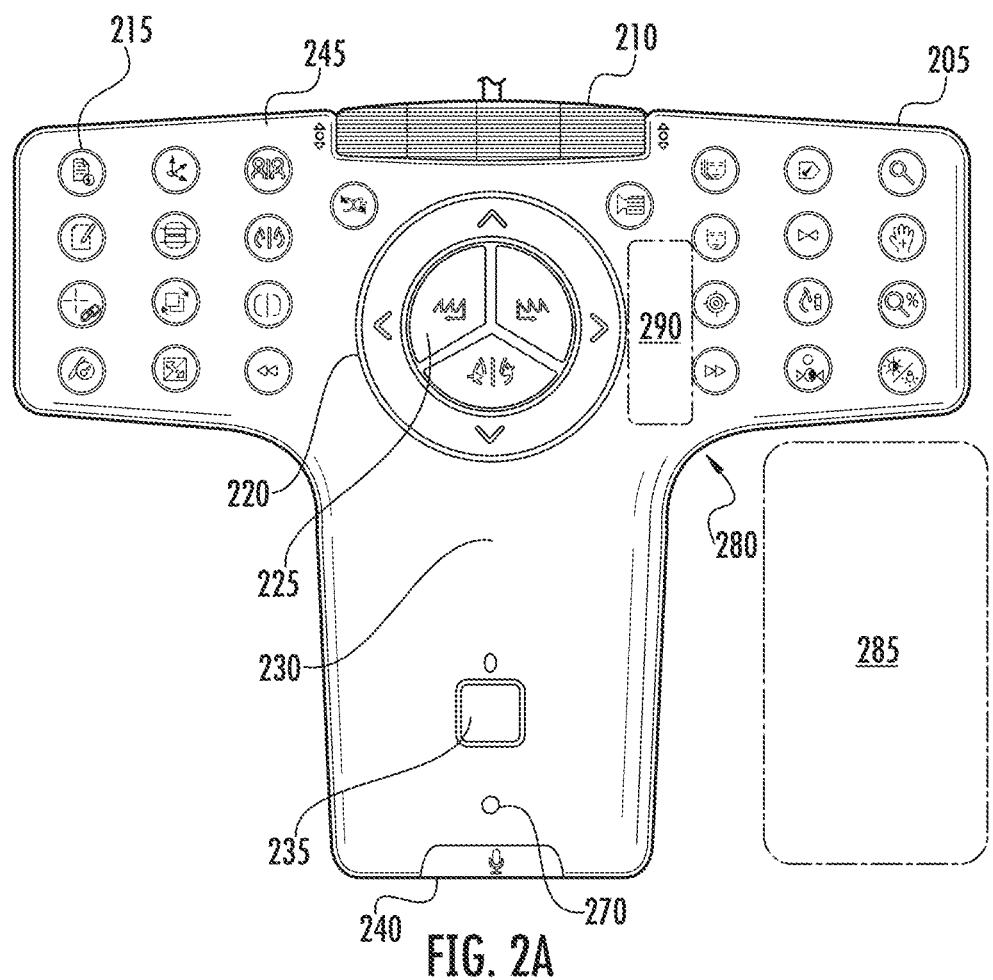
Figure 2B:
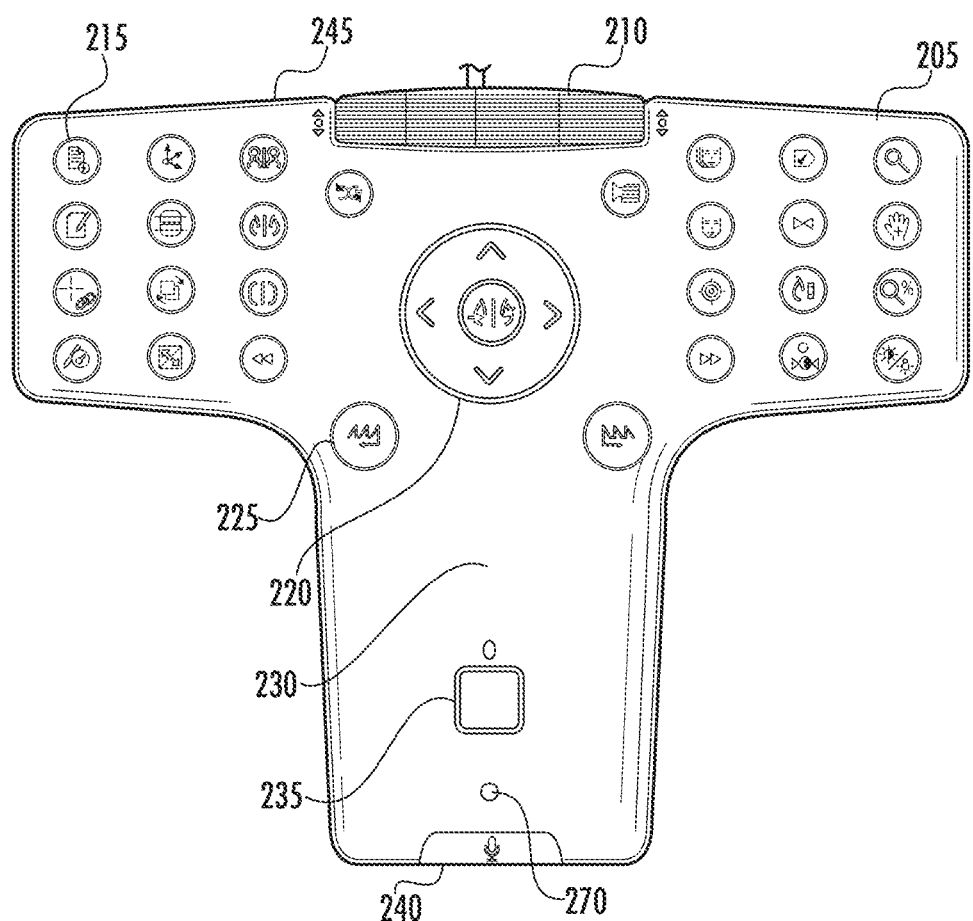

It is appreciated that physical controls and on-screen user interfaces define the way radiologists interact with the workstation. It is further appreciated that various features of the controller 205 described herein have been designed to allow the radiologist to use the controller 205 and the associated workstation over long periods of time without causing discomfort to the radiologist. FIGS. 2A-2J depict various aspects of a controller according to a first embodiment. As shown in FIG. 2A, a controller 205 may include a scroll wheel 210, touch button controls 215, and navigation/diagnostic controls 225. Although controller 205 may include a plurality of touch button controls 215 and/or navigation controls 225, only one is labeled to simplify the figures. Non-limiting examples of navigation/diagnostic controls 225 may include patient flow next/back and/or computer-aided detection (CAD) diagnostic tools. Touch button controls 215 may be configured to provide various functions (see, for example, FIG. 2E) including, without limitation, annotation functions: annotating (e.g., reports, images, and/or the like), marking (e.g., reports, images, and/or the like), linking/lesion tracking, key image marking, reference lines; diagnostic tools: CAD, toggle mammography (MG)/tomosynthesis (TOMO), cine start/stop; patient navigation: flow next/back, previous/next patient, mammography navigator ("MammaNavigator"), patient list, reset, close study, patient information, scroll, finger print; global image tools: overview, views (e.g., axial, sagittal, coronal, and/or the like), MLO current, CC current; and/or tactical image tools: magnify, invert, brightness, pan, zoom, contrast, true size, and/or magnifier. In the embodiment depicted in FIG. 2A, navigation/diagnostic controls 225 may be located within touch/scroll wheel surface. Referring to the embodiment depicted in FIG. 2B, one or more of navigation/diagnostic controls 225 may be located outside of touch/scroll wheel surface.

In some embodiments, the shape and placement or location of the touch button controls and/or navigation/diagnostic controls 225 may indicate the function of the controls. The user may know what function the touch button controls 215 and/or navigation/diagnostic controls 225 performs by touch without having to take the user's gaze off the display. This minimizes the amount of distraction for the user and allows them to perform the task on "auto-pilot," overtime building physical memory of certain tasks and functions. For example, square buttons can be used to control the movement and positioning of motor driven components. Square buttons could be grouped and oriented horizontally or vertically to clarify direction of movement. Round buttons can be used for latch and momentary switches such as Power On and Off, accessory lighting and other inputs. Buttons can be convex or concave to improve tactility and differentiation.

In some embodiments, touch button controls 215 and/or navigation/diagnostic controls 225 may include physical buttons. In some embodiments, touch button controls 215 and/or navigation/diagnostic controls 225 may include capacitive/projected capacitive buttons. Functions associated with touch button controls 215 and/or navigation/diagnostic controls 225 may be activated according to various techniques including, without limitation, momentary activation (e.g., push and release), sustained activation, activation with time threshold (e.g., push and hold for three seconds), and/or the like. The example, the controller can determine a duration of sustained input to one or more of the touch button controls 215, and activate a function associated with the button controls based on the duration being equal to or greater than a threshold.

In some embodiments, functions associated with touch button controls 215 and/or navigation/diagnostic controls 225 may be user-programmable. As discussed above, radiologists are the typical users for the controller and because they use it for prolonged periods of time, develop particular methods of working that are unique to the individual radiologist. Being able to program the button controls and/or navigation/diagnostic controls for use with the individual radiologist's working preference would increase the radiologist efficiencies and allow for greater accuracy. For example, in some embodiments, one or more of the touch button controls 215 and/or navigation/diagnostic controls 225 may include blank keys that may be user defined via a software interface (e.g., interface of healthcare information software application and/or a display screen of controller, such as display screen 310 of controller 305). In one embodiment, the touch button controls 215 and/or navigation/diagnostic controls 225 may display a symbol of the function it performs. The user may redefine the function of the touch button controls 215 and/or navigation/diagnostic controls 225 and the symbol associated with the reprogrammed function may appear to indicate the new function of the touch button control and/or navigation/diagnostic controls 225. In some embodiments, the customizations and preferences are shared between hardware controller and software displayed on the workstation 120. For example, the user may define a function on the software displayed on the workstation and the same function is programmed on the controller 205, such as one of the touch-button controls 215. One example implementation of such a feature can be a programmable touch button control for displaying a patient list when selected on both the controller 205 and the workstation software.

In some embodiments, one or more of scroll wheel 210, touch button controls 215, and/or navigation diagnostic controls 225 may be configured to control various aspects of a user's environment, such as lighting, music, and/or the like. For example, actuation of scroll wheel 210 may operate to change the volume of speakers, adjust monitor brightness, and/or the like.

In some embodiments, functions associated with touch button controls 215 and/or navigation/diagnostic controls 225 may be context-based (i.e., based on a software state) and dynamic. In various embodiments, controller 205 may determine or otherwise be associated with a context. Based on the determined context, the controller 205 displays different touch button controls 215 and/or navigation/diagnostic controls 225 and the different associated functions. The associated different touch button controls 215 and/or navigation/diagnostic controls 225 may control different functionality. Non-limiting examples of context may include software state, imaging modality, window adjustments, dictation mode, where in the imaging workflow, hanging protocol mode of operation, mode of use of workstation, type of health care information, and/or the like. For example, context may include the active function of an application that input from the controller is being sent to, for instance, a healthcare information software application. A context may include a diagnostic image context responsive to the healthcare information software application being used to view a diagnostic image. In another example, a context may include a patient record context responsive to the healthcare information software application being used to view patient records. Accordingly, functions associated with touch button controls 215 and/or navigation/diagnostic controls 225 may be determined based on the context. One example, of context based dynamic controls in shown in FIG. 2K. In this example, image manipulation touch button controls 250a are displayed when the mammography images and reviewing function 255a is accessed by the user on the workstation. The controller 205 detects the context as the mammography image reviewing 255a and dynamically and automatically displays the image manipulation touch button controls 250a that are specific to the mammography context. The image manipulation touch button controls 250a are touch capacitive and are displayed using a back-lit display. When the user selects one of the image manipulation touch button controls 250a the controller 205 received that input and sends the associated commands to the workstation. Similarly, when the user accesses an MRI image via the workstation, the controller 205 detects that an MRI image or functionally is accessed and automatically and dynamically changes the context based touch button controls 215 to displays the MRI control buttons 250e on the controller 205. The controller 205 receives the input from the user selecting one of the MRI buttons 250e and performs the associated function on the workstation. The dynamic context detection functionality can function to be sequential, transitioning from a first context based set of touch button controls to a second context based set of touch button controls to a third set of touch button controls.

In some embodiments, some or all of the touch button controls 215 can change based on receiving a specific user input, such as receiving the selection for an MRI or Ultrasound image displays the MRI or Ultrasound image controls 250e or 250f from image manipulation controls 205a. In other embodiment, some or all of the touch button controls 215 can change based on pre-programmed set of logic functions that anticipate the next step in the workflow of the radiologist user, such as for example, determining whether the user is examining a particular section of the screen (i.e. determining a hover function input from a user) in the image navigation workflow 255c, the controller 205 changes the touch button controls 215 to be the annotation controls 250c to anticipate the user desiring to access the annotation functionally. Embodiments are not limited in this context.

Referring to FIG. 2A, in some embodiments, controller 205 may include a touch/scroll wheel surface 220. In some embodiments, touch/scroll wheel surface 220 may include a capacitive touch element configured to provide touch-based scroll wheel functionality to controller 205. In contrast, scroll wheel 210 may include a wheel element requiring physical manipulation (for instance, via rotation) to activate corresponding input. In some embodiments, manipulation of scroll wheel 210 and/or touch/scroll wheel surface 220 may activate various features, functionality, and/or navigation functions. For example, either of rotational (e.g., rotating a finger around the surface of touch/scroll wheel surface 220) or directional motion (e.g., pressing a directional element of touch/scroll wheel surface 220) of touch/scroll wheel surface 220 may activate various features, functionality, and/or navigation functions. The scroll wheel 210 may be similar to the scroll wheel 720 as further shown and described in FIG. 7C. In another example, forward rotational motion of touch/scroll wheel surface 220 (e.g., rotating a finger around the surface of touch/scroll wheel surface 220 in a clockwise motion) may cause a healthcare information software application to scroll through a series of images in a first direction, while backward rotational motion (e.g., counter-clockwise motion) may cause the healthcare information software application to scroll through the series of images in a second direction. Embodiments are not limited in this context.

Figure 2C:
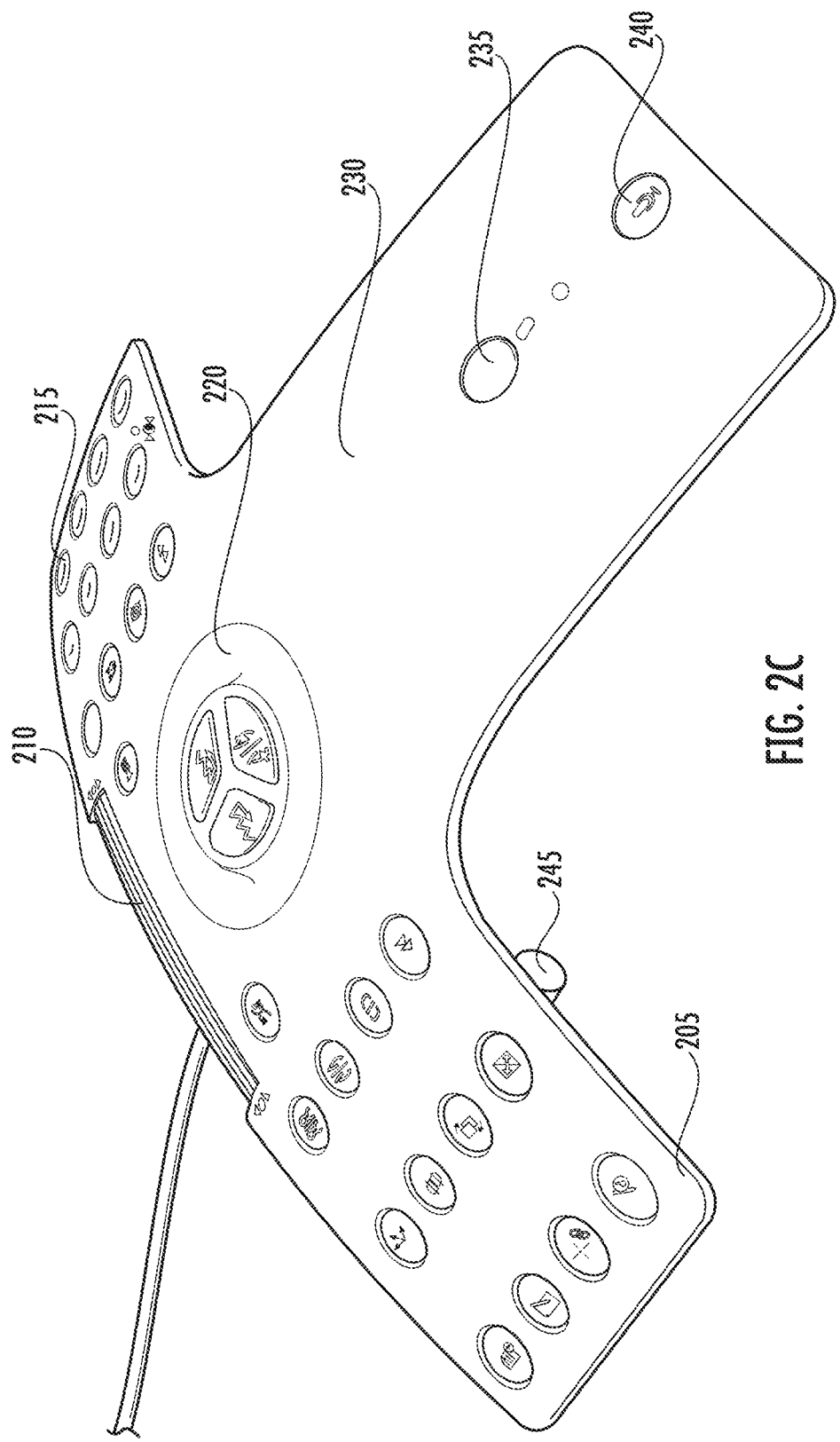

In various embodiments, controller 205 may include a microphone 270, for example, for providing dictation functionality. Microphone 270 may be controlled (for example, activated) using a microphone control button 240. The microphone control may be configured to provide control signals to a workstation computing device 135 executing a software dictation application. In some embodiments, controller 205 may include various security features to only allow authorized users to operate controller 205 and/or certain features of controller 205. Accordingly, in some embodiments, controller 205 may include a biometric element 235 for authenticating users. In various embodiments, biometric element 235 may include a fingerprint reader. As shown in FIG. 2C, controller may include various ports 245 for coupling controller 205 to various devices, such as computing devices, electronic devices, and/or the like. In at least some embodiments, the controller 205 may control multiple workstations 120. In some examples, the controller may be physically connected to different workstations 120 via the ports 245, in other examples, the controller 205 may be wirelessly connected. The controller may include a touch button that allows the controller 205 to switch between control of the different workstations 120.

In some embodiments, port 245 may include a microphone jack, a headphone jack, and/or the like. In some embodiments, port 245 may include a port configured according to various communication protocols, such as universal serial bus (USB). In some embodiments, port 245 may be configured to operate as a hub (e.g., a USB hub). Controller 205 via port 245 may be configured to interface with various devices including, without limitation, a bar code reader, a microphone, headphones, a computing device, a portable storage device, and/or the like. Although a single port 245 is depicted on the front of controller 205, embodiments are not so limited as controller 205 may include a plurality of ports 245 arranged in various locations on controller 205 (see, for example, FIG. 2C).

In various embodiments, controller 205 may include a palm rest area 230 configured to receive a palm of a hand of a user engaged in manipulating controller 205, for instance, via scroll wheel 210 and/or touch button controls 215. Controller 205 may be formed to be substantially T-shaped, for instance, including inwardly-contoured side sections 280 to allow for negative space 285 immediately adjacent to controller. In this manner, an operator may maintain certain objects, such as a keyboard, documents, mobile computing devices (e.g., smartphone or tablet computing device), and/or the like in a nearby and convenient location on a work surface while using controller 205. In addition, an unpopulated area 290 may be included on any portion around the scroll wheel 220, such as one or both sides of scroll wheel 220, to provide for a finger rest for one or more fingers of a hand manipulating scroll wheel 220. In general, areas of controller 205 configured as "rest areas" (for instance, palm rest area 230 and/or unpopulated area 290) may be configured around functional interfaces (for instance, scroll wheel 210 and/or touch button controls 215) while allowing a portion of a hand to rest without activated a function. For example, if there is an annulus for scroll wheel 210, then there may be "dead space" (i.e., an area devoid of functional elements) around or immediately adjacent to allow for a portion of a hand (e.g., a palm or finger) to rest on the controller 205. In addition, the form of controller 205 (as well as controllers 305, 505, and 605, described below) and the location and form of landmark objects (e.g., home positions, rest areas, and/or the like) on controller may provide strong physical reference points to allow an operator to efficiently and effectively operate controller 205 without looking at controller 205. Non-limiting examples of physical reference points may include a palm rest, varying button height, contrasting materials, button demarcations (e.g., a physical mark or other protrusion on a button), button shapes, and/or physical button locations. Furthermore, in some embodiments, controller may be configured as a six degree of freedom input devices (e.g., a "6 DoF puck") to allow for the control and/or navigation of 3D data sets, including MR images. On a functional level six degree of freedom controllers may combine pan, tilt/rotate and zoom capabilities of software into one hardware control. For instance, a six degree of freedom controller may allow for free and natural movement of 3D models in 3D space without necessitating a modal change between pan and tilt/rotate, for example. In some embodiments, controller 205 (as well as controllers 305, 505, and 605, described below) may support use of a second controller (e.g., a mouse or keyboard) using a hand not being used to operate controller 205. For example, a right-handed individual may operate 205 using a left hand while also interacting with an application via a mouse using their right hand, or vice versa.

Figure 2D:
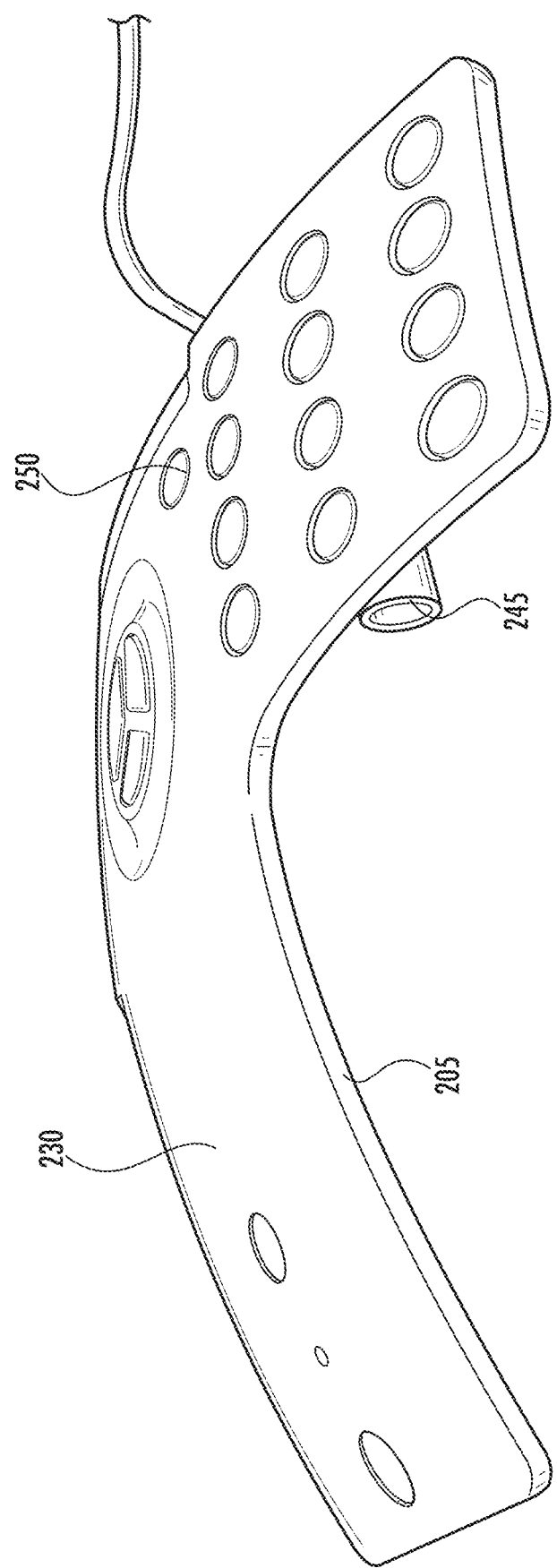

Referring to FIG. 2C, therein is depicted controller 205 according to some embodiments. As shown in FIG. 2C, controller may include various ports 245 for coupling controller 205 to various devices, such as computing devices, electronic devices, and/or the like. In some embodiments, port 245 may include a microphone jack, a headphone jack, and/or the like. In some embodiments, port 245 may include a port configured according to various communication protocols, such as universal serial bus (USB). In some embodiments, port 245 may be configured to operate as a hub (e.g., a USB hub). Controller 205 via port 245 may be configured to interface with various devices including, without limitation, a bar code reader, a microphone, headphones, a computing device, a portable storage device, and/or the like. Although a single port 245 is depicted in a particular location on the controller 205 illustrated in FIG. 2C, embodiments are not so limited as controller 205 may include a plurality of ports 245 arranged in various locations on controller 205 (see, for example, FIG. 2A). FIG. 2D depicts a side-view of controller 205 according to some embodiments. As shown in FIG. 2D, controller 205 or portions of controller 205 may have a concave or substantially concave shape. In this manner, controller 205 may provide ergonomic support to a hand of an operator during use of controller 205.

Figure 2E:
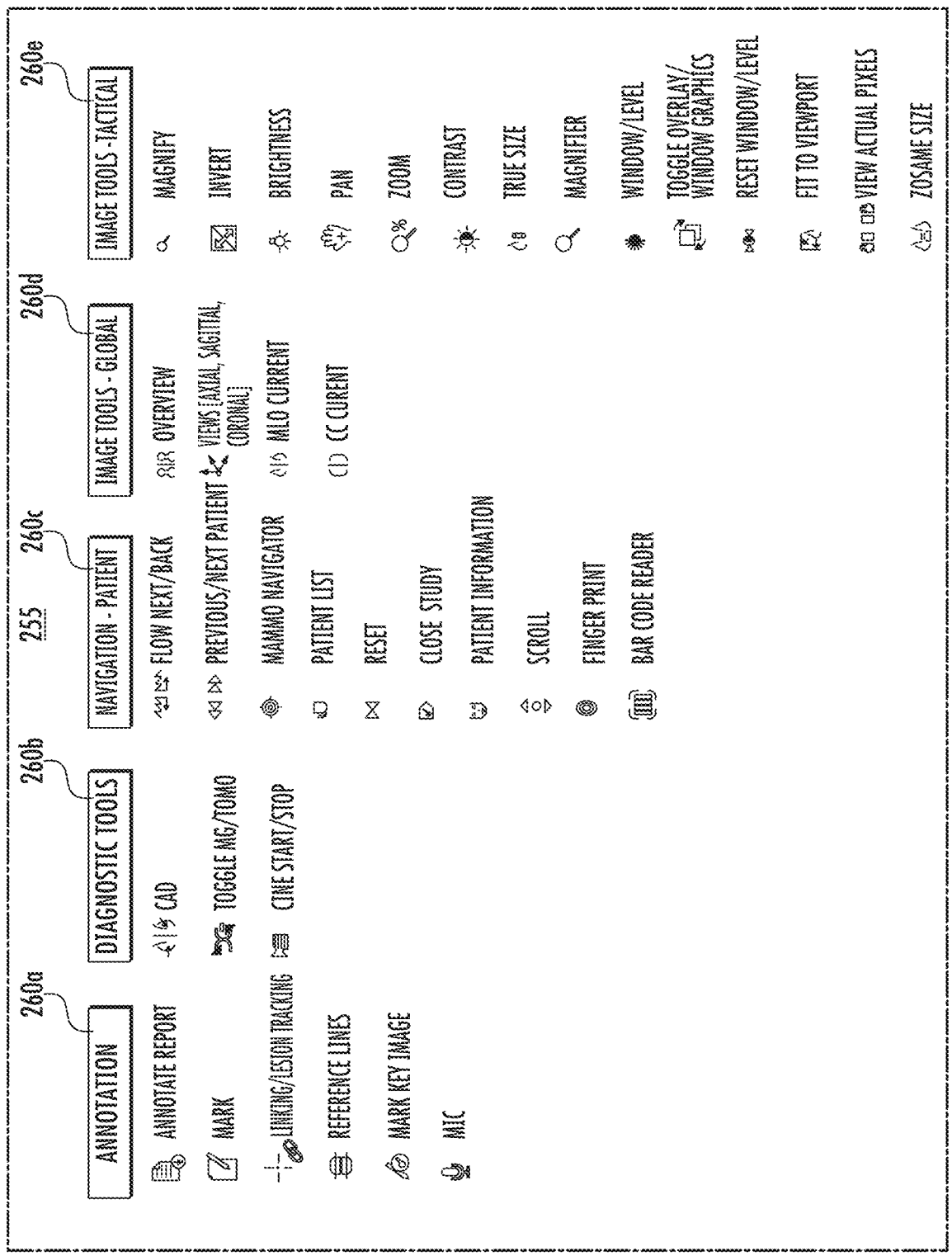

In some embodiments, various control elements of controller 205 may be grouped according to functionality. FIG. 2E depicts functional groupings 255 for controller 205 according to some embodiments. In some embodiments, functional groupings 255 may allow for sequential operation of functionally grouped controls (i.e., masking, guidelines, inverting, subtractions, and/or the like). As shown in FIG. 2E, controller may include an annotation functional grouping 260a, a diagnostic tools functional grouping 260b, a navigation-patient functional grouping 260c, an image tools-global functional grouping 260d, and/or an image tools-tactical functional grouping 260e. The groupings are organized and placed on the controller based on a number of factors, including ranking of functions most commonly or most often used by radiologists as well as based on specific functionality. The annotation function grouping 260a includes functions that allow the radiologist to annotate an image with notes, for example marking a section of the image with a tool to highlight a suspicious region, adding a comment, linking an area between one or more images. Diagnostic tool grouping 260b includes functions that include additional diagnostic modules, functionality or software, such as CAD (computer-aided detection) that runs a software application that identifies and marks regions of interest on routine screening and diagnostic mammograms to bring them to the attention of the radiologist after the initial reading has been completed. Navigation-Patient grouping 260c includes various functions that are used throughout the workstation software to view, navigate and review general information. These tools can be universal or more general and can be used throughout different functionalities, such as patient lists, patient information, next and previous stepping functions. Image Tools-Global 260d include the image tools that allow the radiologist to review the patient image information or case study at the global level. For example, inventors have appreciated that radiologists review the images available to them for review at a global level before reviewing the images at the local or tactical level. Similar to reviewing the table of contents in a book with chapter heading before proceeding to read the individual chapters and contents thereof, the radiologists prefer to review the image overview and history of the patient, prior to accessing the individual images. Some radiologist flip back to the overview throughout the case analysis. Image Tools-Tactical 260e include the local or tactical image tool that manipulate the images on the individual level. Embodiments are not limited in this context.

The functional grouping described above may be grouped together using homing features as further described below with reference to FIG. 7D. For example, grouping tactical images tools together using vertical physical grooves and grouping navigation tools together using horizontal grooves.

Figure 2F:
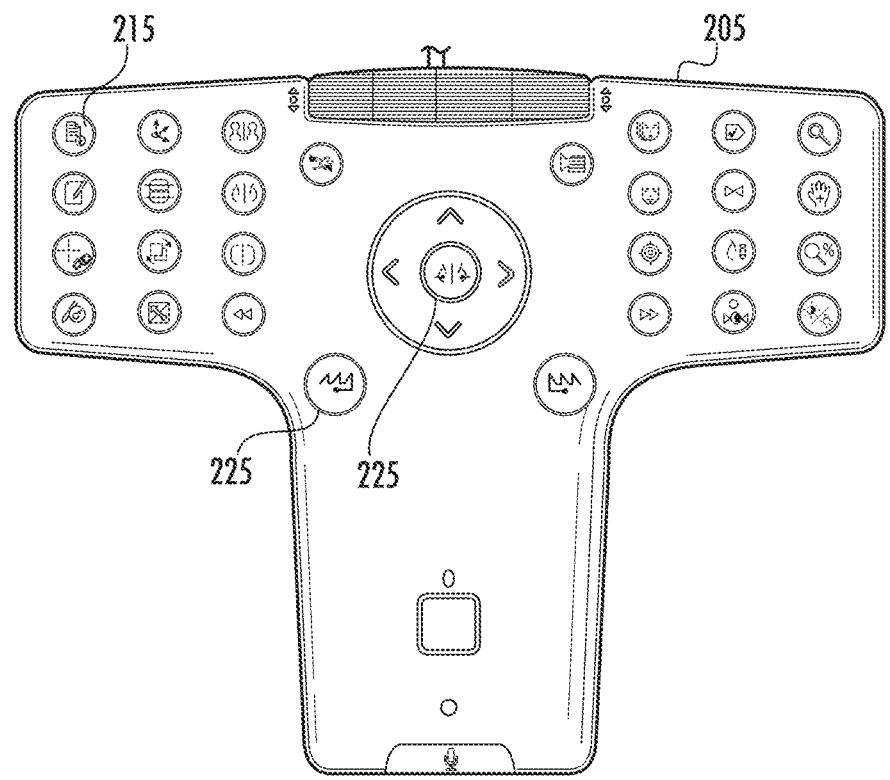
Figure 2G:
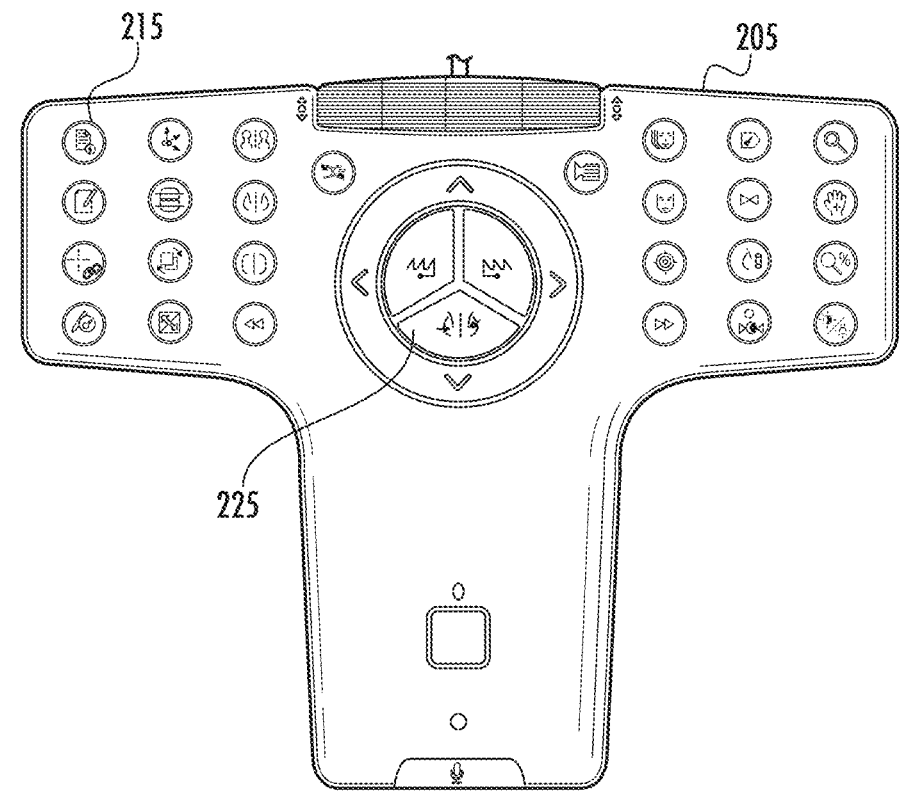

FIGS. 2F and 2G depict controller functional grouping according to some embodiments. In some embodiments, the functional groupings 255 may be applicable to user-programmable controls, context-based controls, and/or combinations thereof. As described above in reference to context-based controls, some grouping may dynamically change based on the context while others may be permanently placed in their locations on the controller 205. In addition, the groupings may be placed in physical locations on the controller 205 where they are more or less frequently used. For example, FIGS. 2F and 2G depict placement of diagnostic tools closer to the center of the controller while keeping annotation tools farther away from the center of the controller. Embodiments are not limited in this context.

Figure 2H:
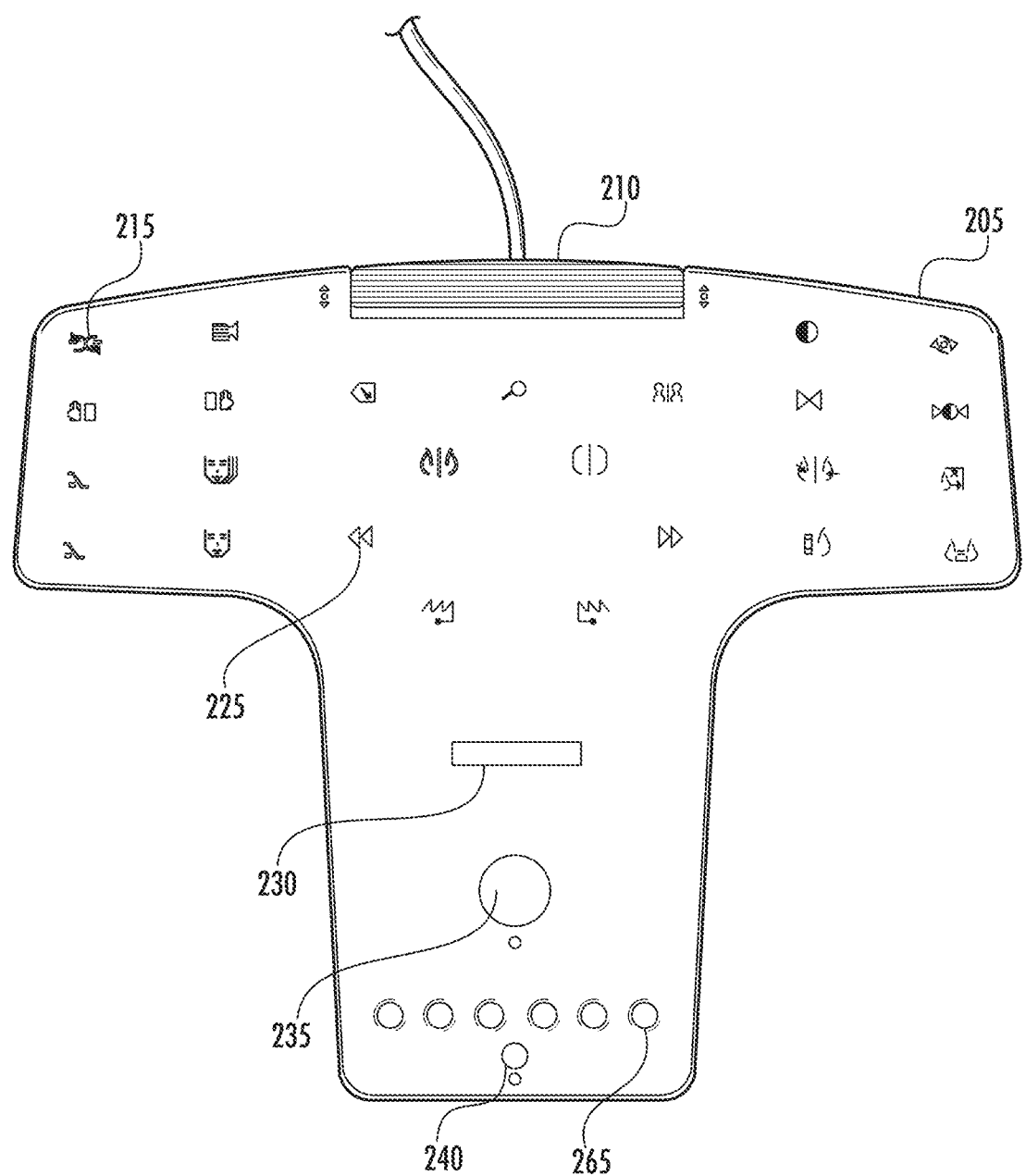
Figure 21:
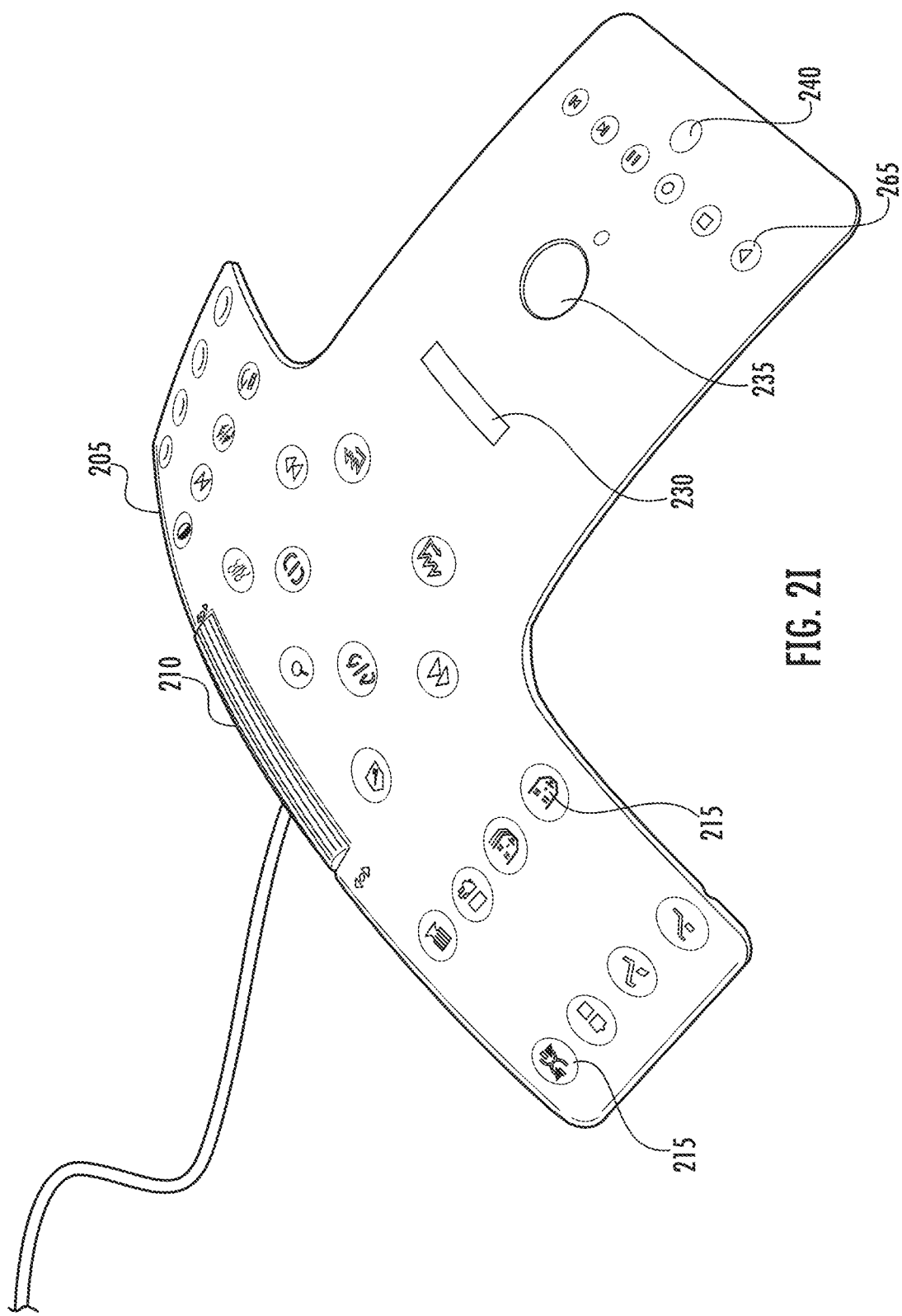
Figure 2J:
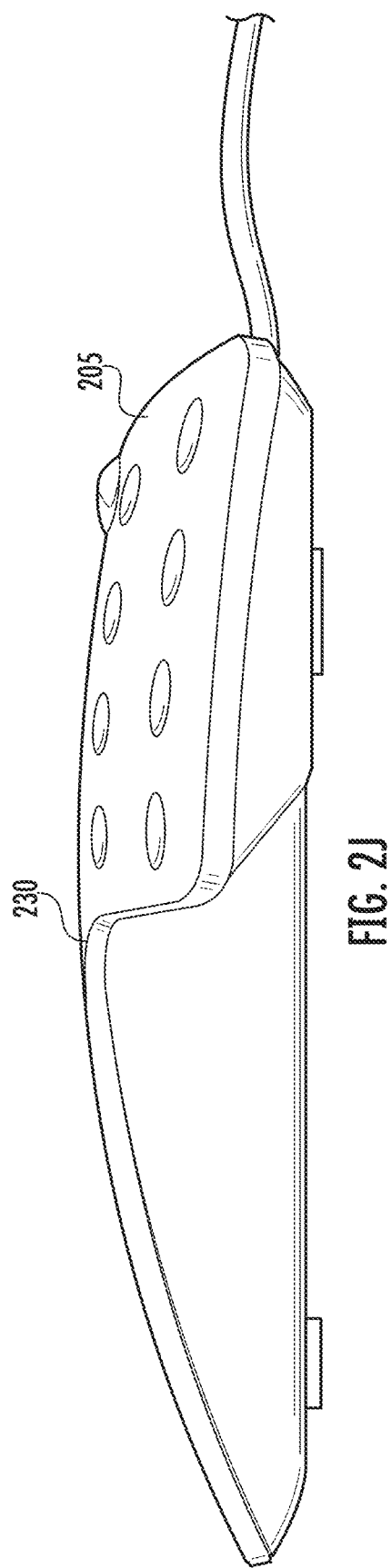
Figure 2K:
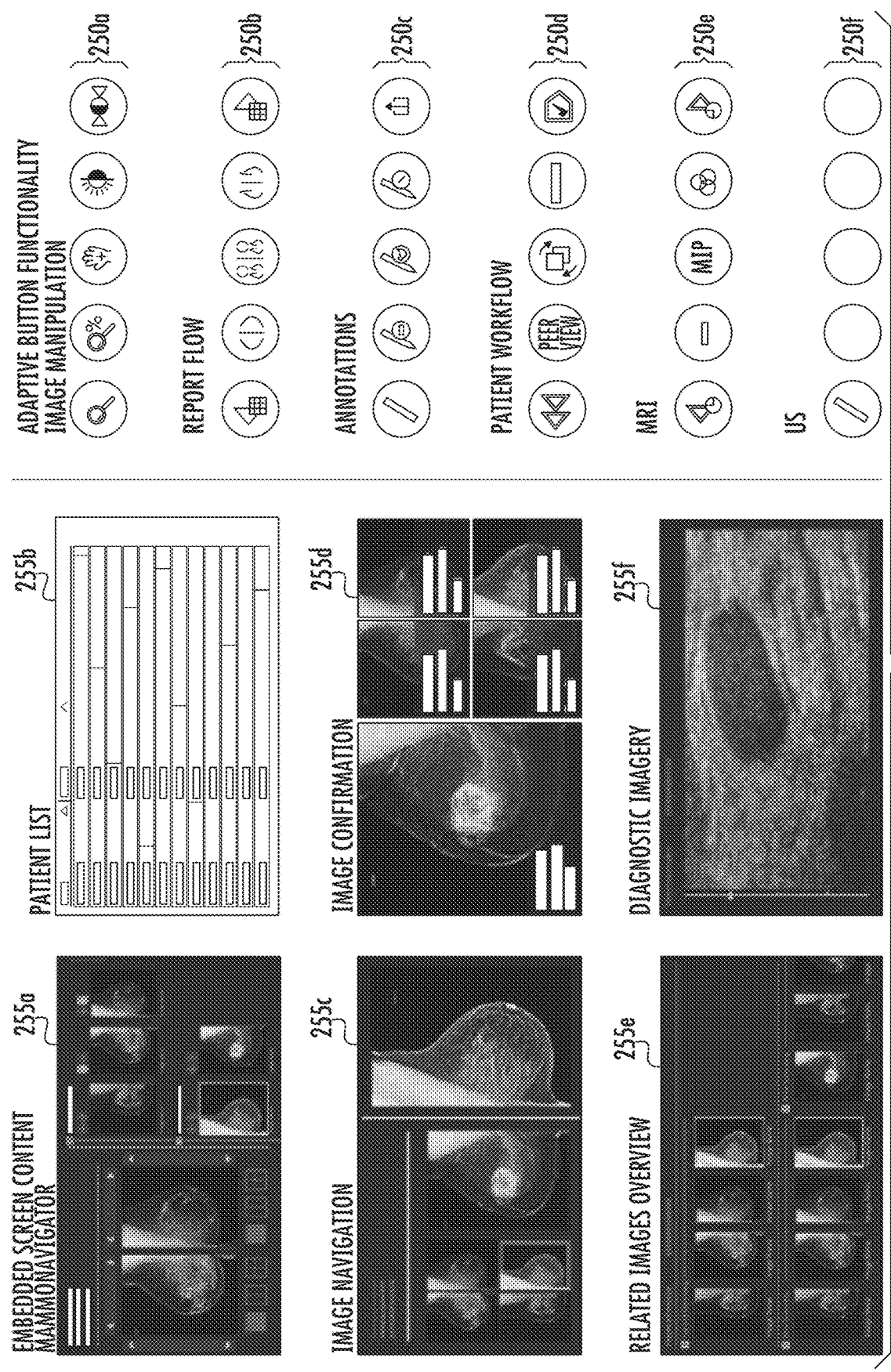

FIG. 2H depicts a first top-down view of a controller 205 according to some embodiments. As shown in FIG. 2H, controller 205 may include various dictation controls 265, for instance, located adjacent to microphone control button 240. In some embodiments, the dictation controls 265 and/or the microphone control button 240 may be default or fixed controls, user-programmable controls, and/or context-based controls. For example, the dictation controls 265 may be activated, programmed, or otherwise made available responsive to a healthcare information annotation screen being presented (for instance, via monitor 130 of workstation computing device 135). FIG. 2I depicts a second top-down view of controller 205 according to some embodiments. In FIG. 2J, a side view of controller 205 is depicted according to some embodiments. As shown in FIG. 2J, controller 205 may be configured to arc downward from a high point to a low point in opposite directions from palm rest 230 to provide enhanced ergonomic support of a hand of user manipulating controller 205.

Figure 3A:
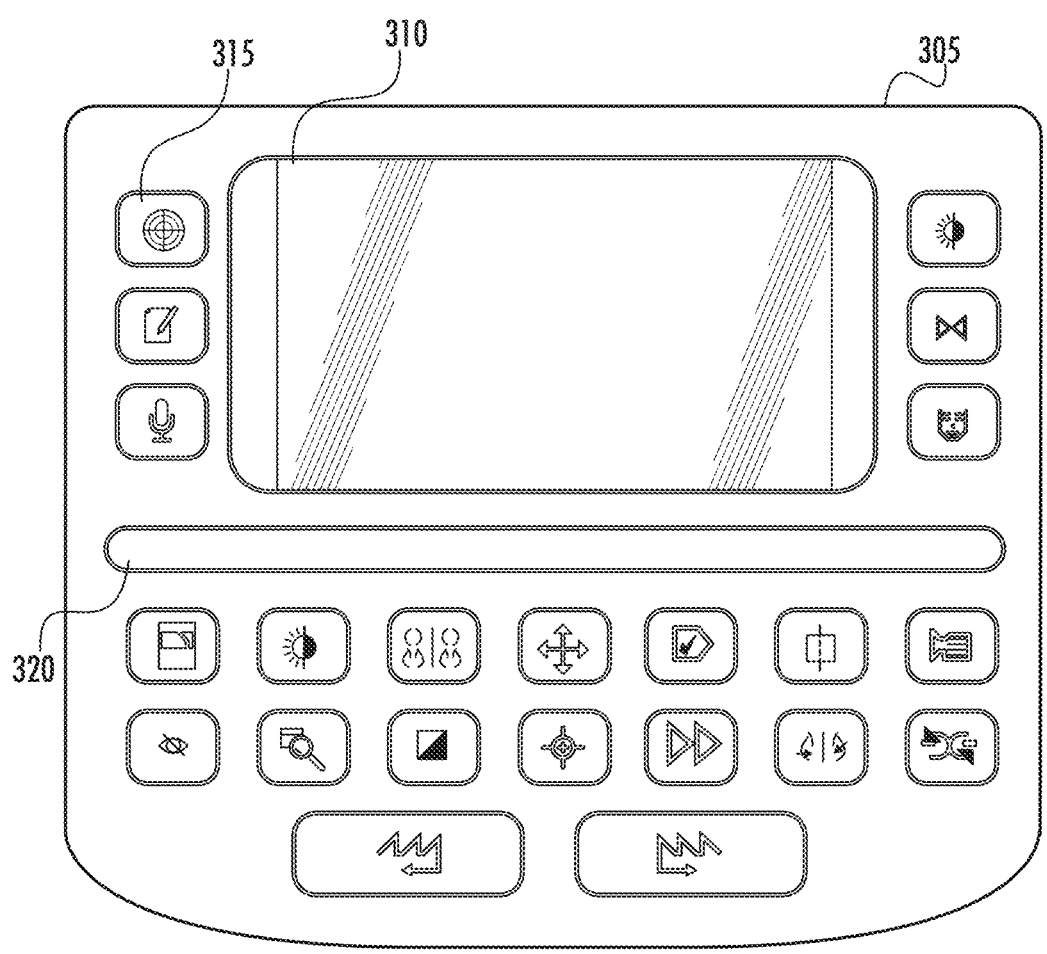
FIGS. 3A-3J depict various aspects of a healthcare information controller according to a second embodiment.

FIGS. 3A-3J depict various aspects of a controller according to a second embodiment. Referring to FIG. 3A, therein is depicted a controller 305 that includes a plurality of touch button controls 315, a scroll control 320, and a display screen 310. Although controller 305 may include a plurality of touch button controls 315, only one is labeled to simplify the figures. In some embodiments, scroll wheel 320 may include a capacitive touch scroll control. In various embodiments, scroll control 320 may be recessed within a surface of controller 305, for example, for scrolling through TOMO slices. Touch button controls 315 and/or scroll control 320 may have various characteristics according to some embodiments. For example, one or more of touch button controls 315 and/or scroll control 320 may be context-based according to some embodiments. In various embodiments, the relevant context for context-based touch button controls 315 and/or scroll control 320 may be based on an active healthcare information software application, information presented via display screen 310, and/or combinations thereof. In some embodiments, one or more of touch button controls 315 and/or scroll control 320 may have various physical characteristics, such as being formed of various materials, different sizes, different contours (for instance, concave, convex, and/or the like), different heights (for instance, recessed, raised, and/or level with a surface of controller 305), and/or the like. Embodiments are not limited in this context.

In various embodiments, display screen 310 may include a touch screen, for example, a multi-touch enabled screen. In some embodiments, display screen 310 may be configured to provide an embedded graphic display to aid in annotation and to provide an additional display for viewing third-party related healthcare information (e.g., RIS and notation software), for example, without requiring an operator to look away or requiring posture change. In addition, secondary screens (see, for example, FIGS. 4A-4D) may enhance operator workflow when used with multiple palettes, when switching between applications, for reference or comparison, and/or the like.

Figure 3B:
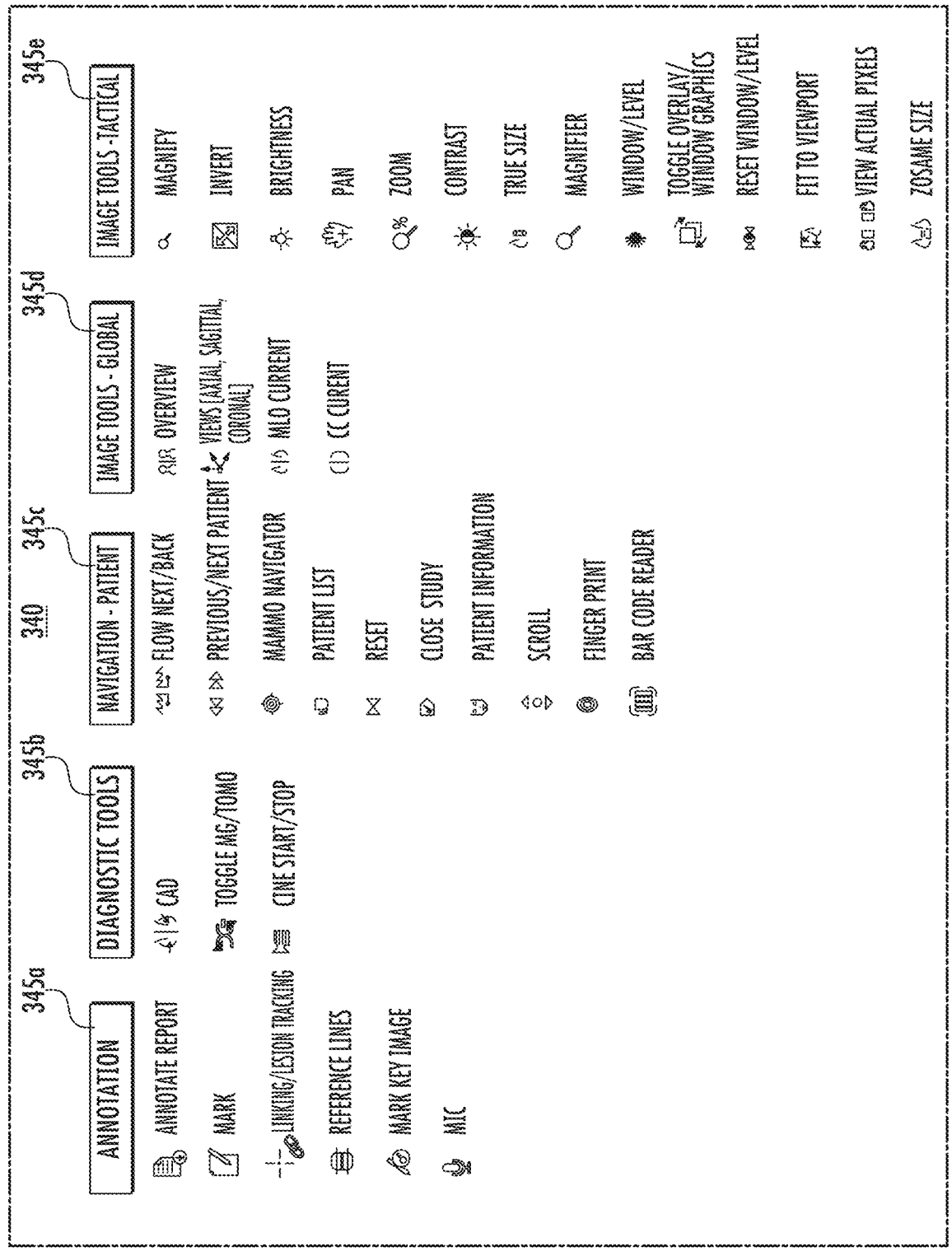
Figure 3C:
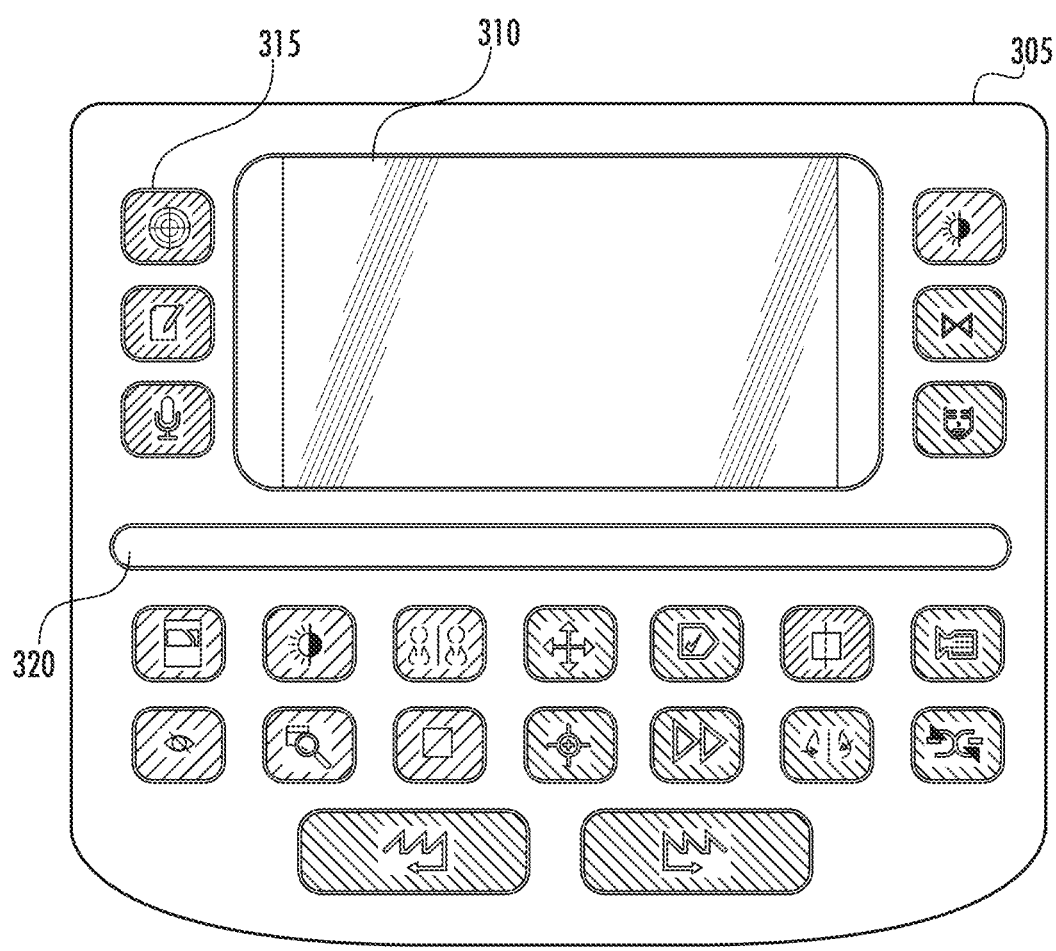

In some embodiments, various control elements of controller 305 may be grouped according to functionality. FIG. 3B depicts functional groupings 340 for controller 305 according to some embodiments. As shown in FIG. 3B, controller may include an annotation functional grouping 345a, a diagnostic tools functional grouping 345b, a navigation-patient functional grouping 345c, an image tools-global functional grouping 345d, and/or an image tools-tactical functional grouping 345e. FIG. 3C depicts controller functional grouping according to some embodiments.

Figure 3D:
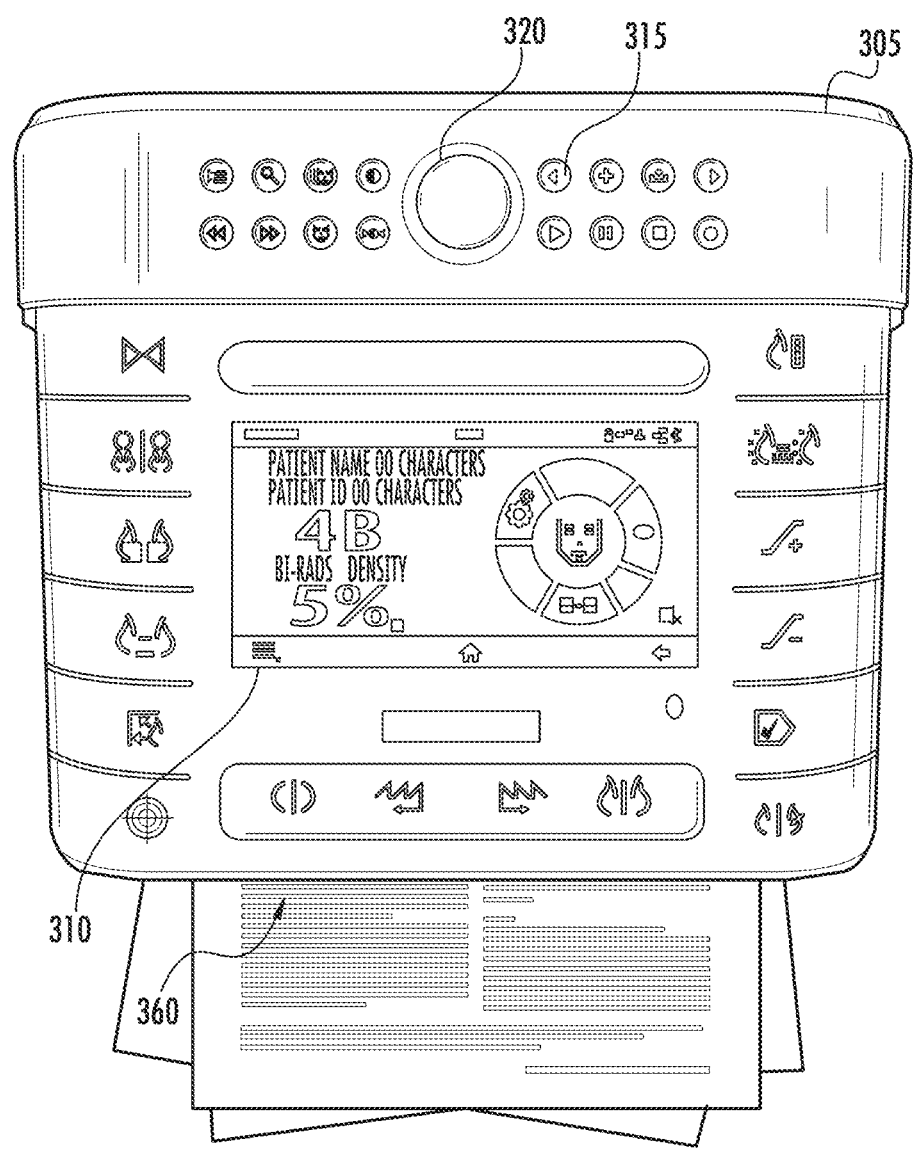

FIG. 3D depicts a top-down view of controller 305 according to some embodiments. In the embodiment depicted in FIG. 3D, controller 305 may have a concave shape such that a space 360 is provided under controller. In this manner, various objects (for instance, documents, mobile computing devices, and/or the like) may be maintained on a working surface beneath or partially beneath controller 305.

Figure 3E:
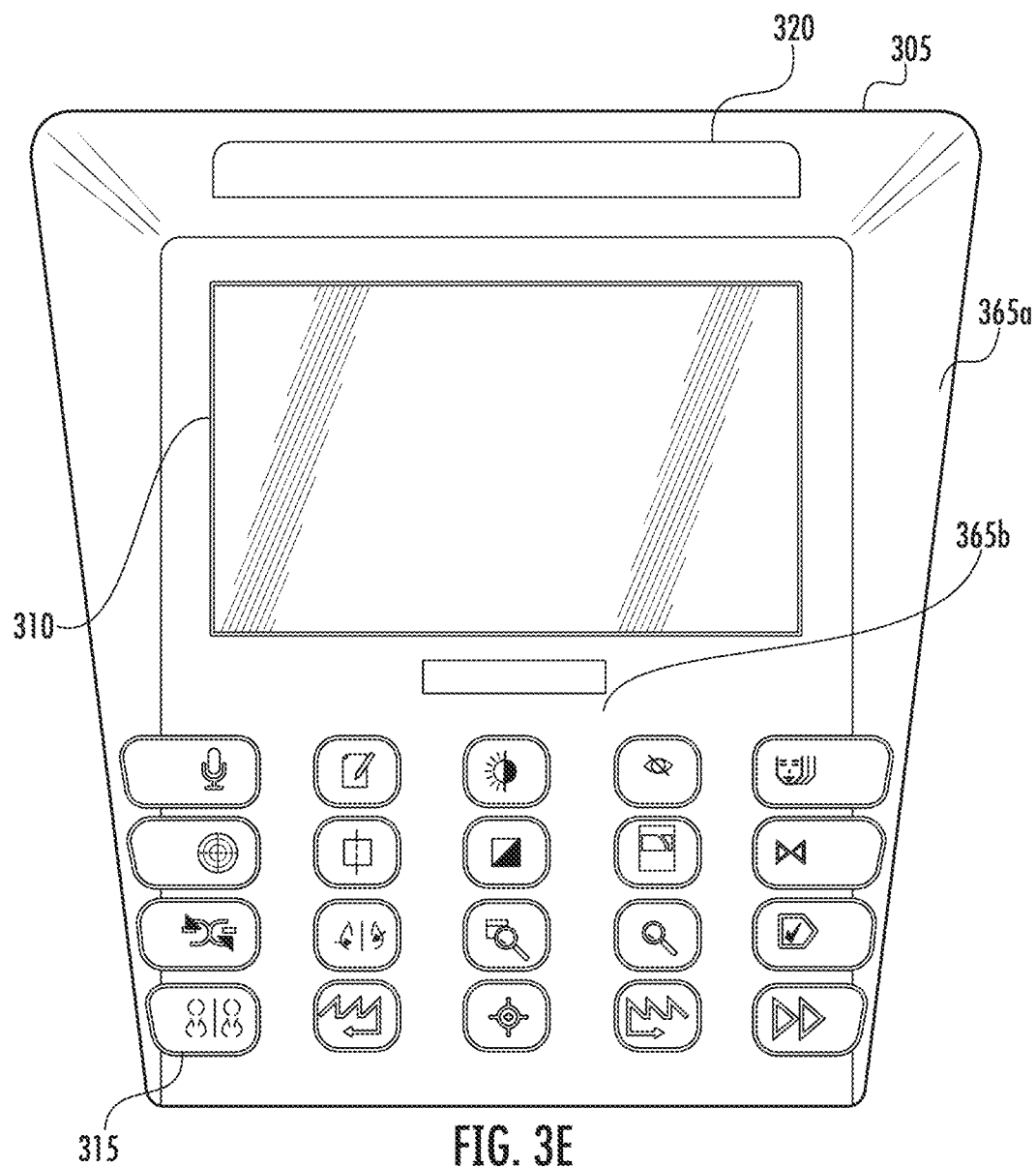
Figure 3F:
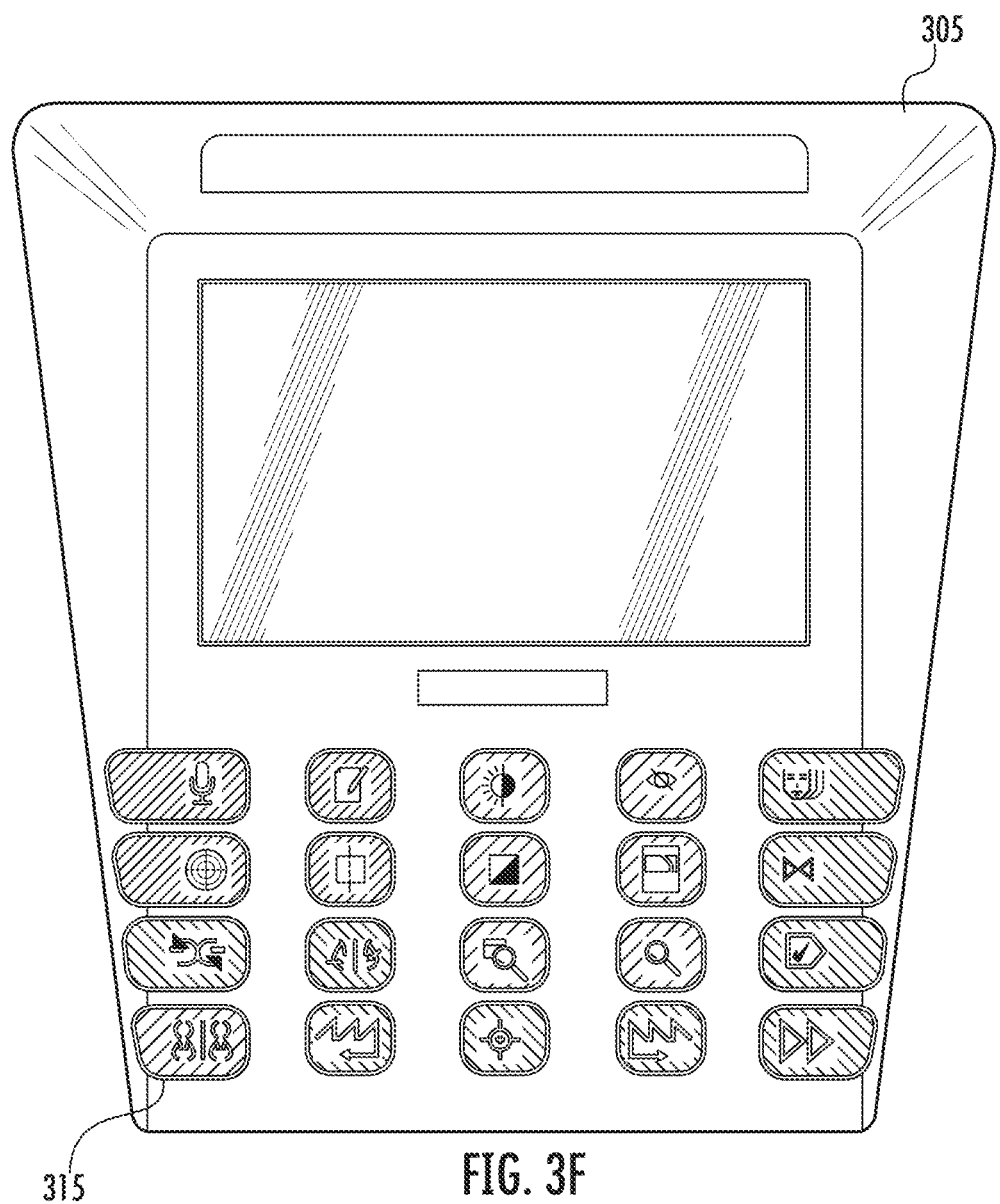
Figure 3G:
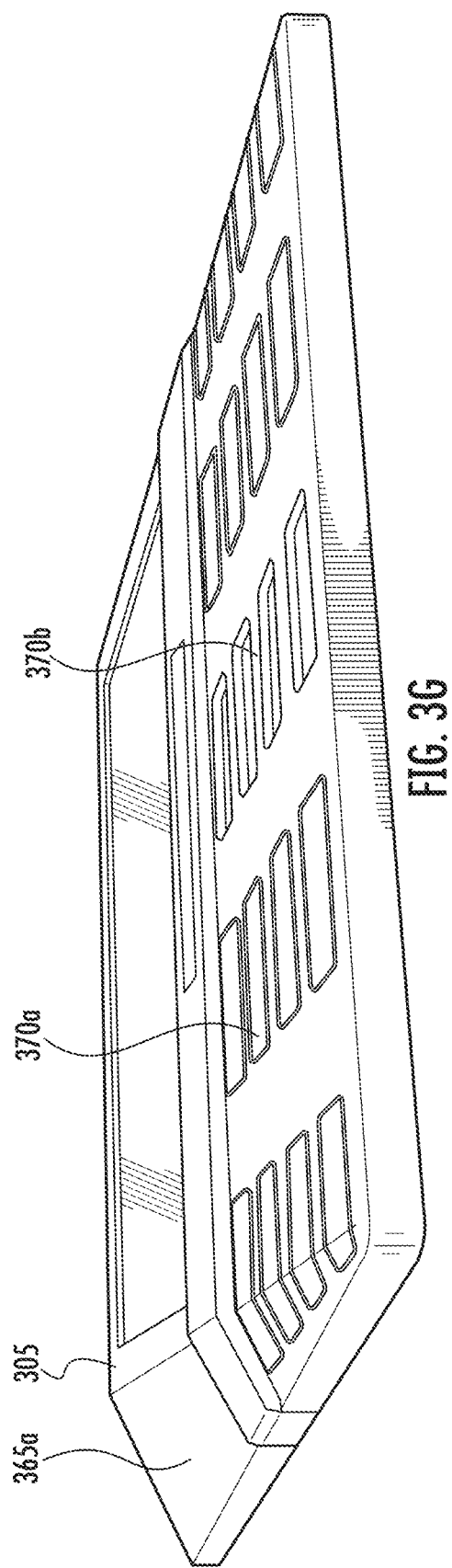
Figure 3H:
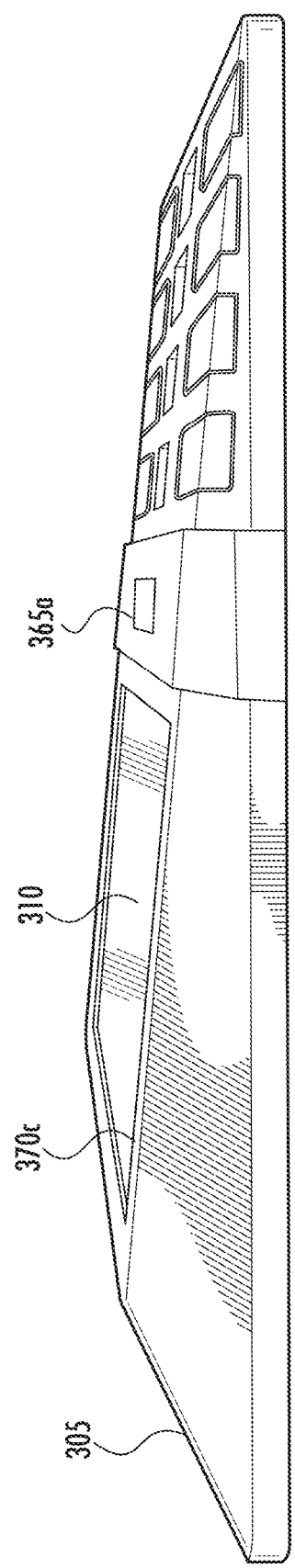
Figure 3I:
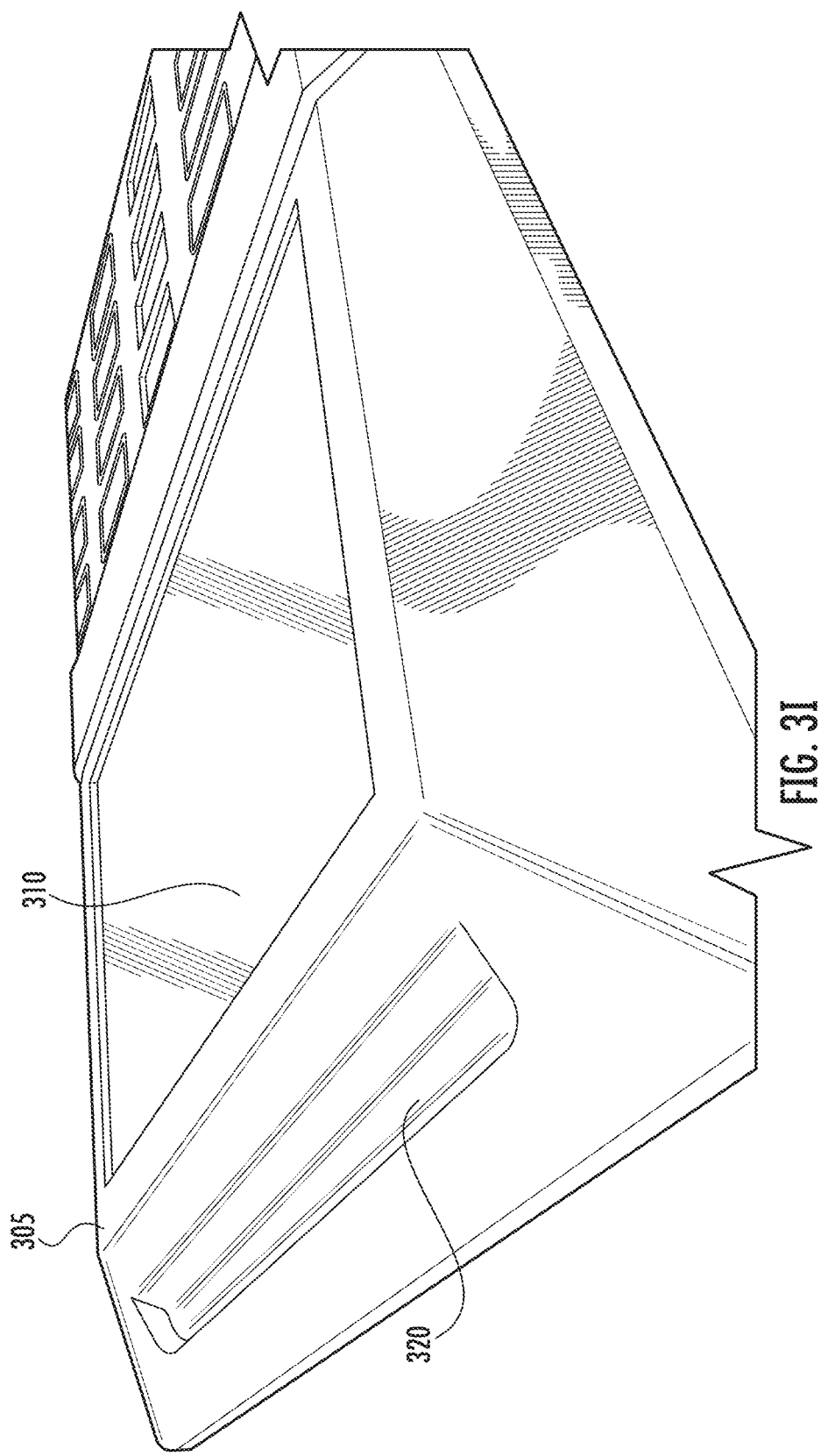
Figure 3J:
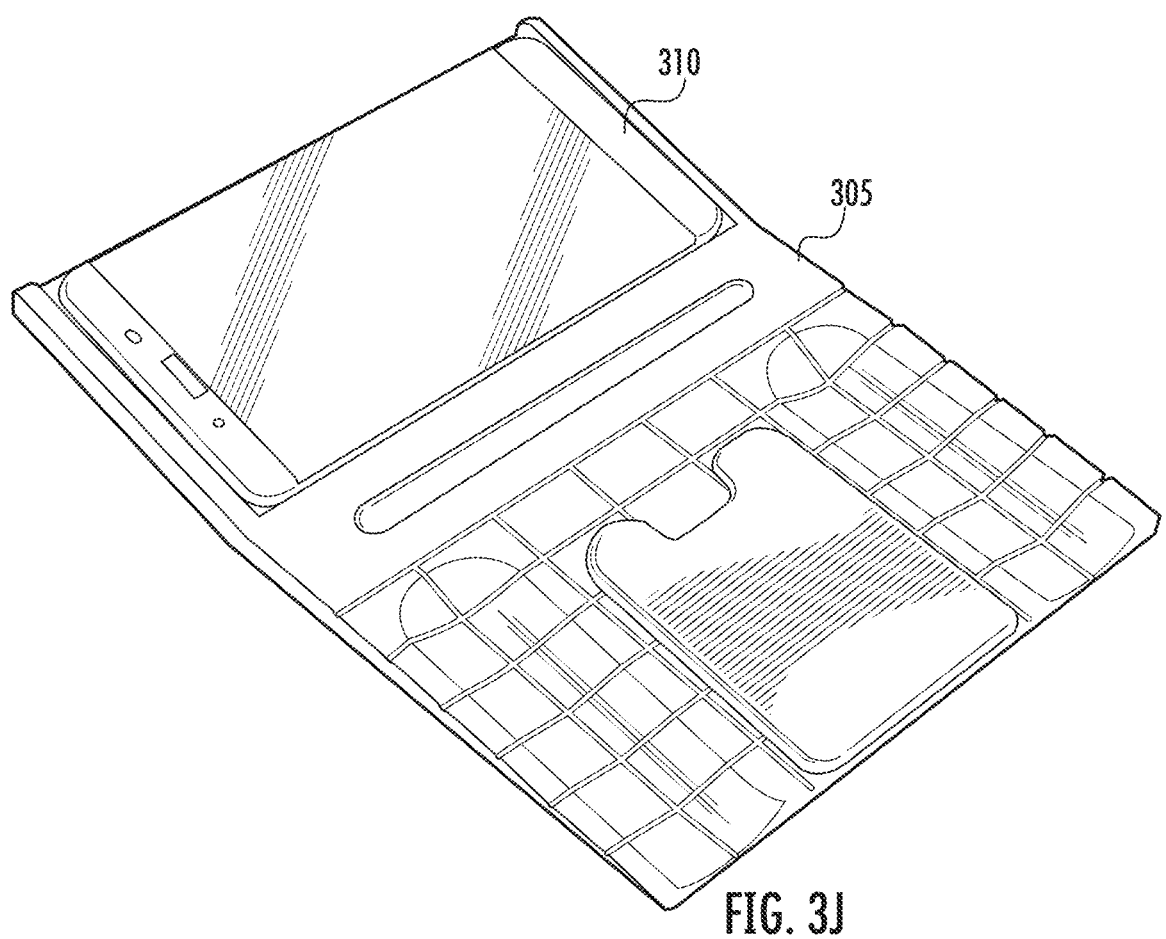

FIG. 3E depicts a top-down view of controller 305 according to some embodiments. As shown in FIG. 3E, controller may include scroll control 320 at a top portion of controller. In addition, controller 305 may be formed to include hand rest areas 365a and 365b for an operator to rest portions of a hand during operation of controller 305. In some embodiments, controller 305 include a side palm rest 365a and a raised palm rest area 365b to elevate a hand of an operator above the surface of the controller 305. FIG. 3F depicts controller functional grouping of the controller 305 depicted in FIG. 3E according to some embodiments. FIG. 3G depicts a front, partial top-down view of controller 305 configured according to some embodiments. As shown in FIG. 3G, the configuration of controller 305 may provide various features 370a and 370b to a user of controller 305, such as a slim form factor 370a and/or varying button heights 370b. FIG. 3H depicts a side view of controller 305 according to some embodiments. As shown in FIG. 3H, controller may include an angle feature 370c in which the display screen 310 is angled toward the user to facilitate viewing of displayed information, prevent glare, and/or the like. FIG. 3I depicts a back, partial top-down view of controller 305 configured according to some embodiments. As shown in FIG. 3I, controller 305 may include a scroll wheel 320, such as a capacitive touch scroll wheel, on a top portion thereof. In various embodiments, touch input for display 310 may be inactive (for instance, touch by a palm or other portion of a hand may not be perceived as input) if a user is using scroll wheel 320 so that, for instance, display 310 may operate as a palm rest area. In some embodiments, controller 305 or portions thereof, such as display screen, may be angled to act as a hand rest for scroll wheel 320. FIG. 3J depicts controller 305 configured according to some embodiments. As shown in FIG. 3J, display screen 310 may include a screen of a mobile computing device, such as a smartphone. In some embodiments, a mobile computing device may be communicatively coupled to controller 305 to allow controller 305 to display information view the display screen of the mobile computing device.

Figure 4B:
Figure 4C:
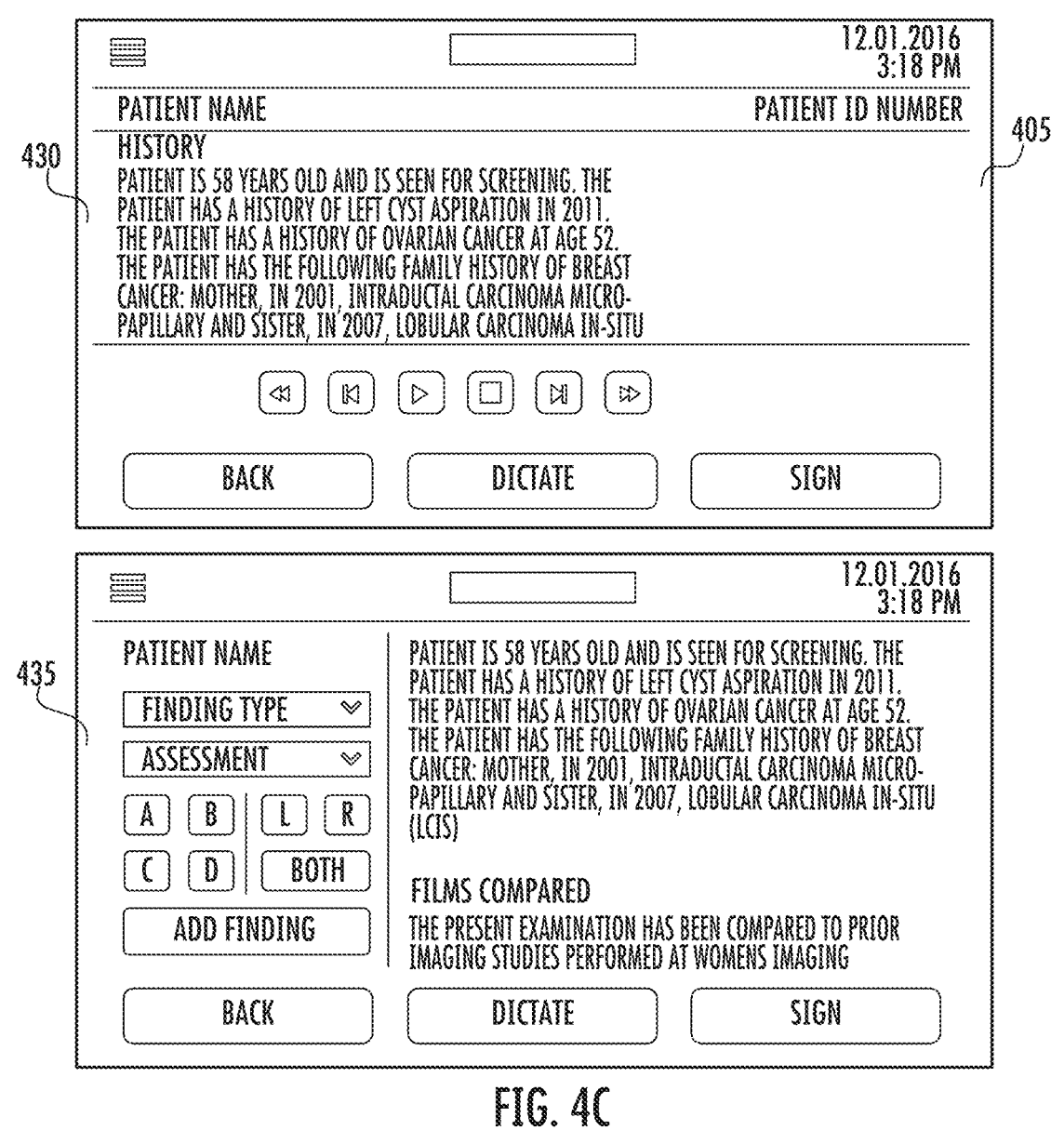
Figure 4D:
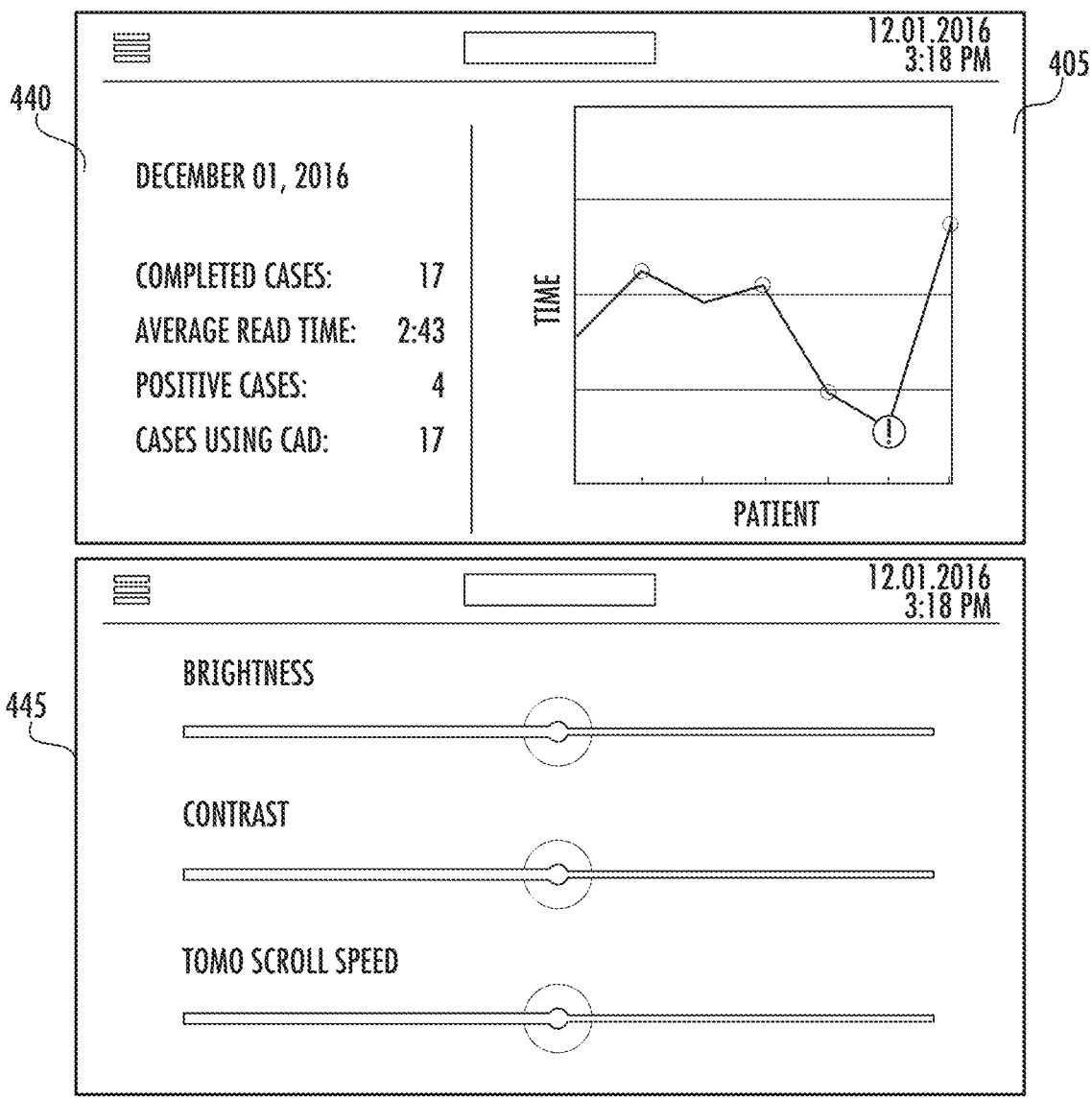

FIGS. 4A-4D depict controller display screens according to some embodiments that may be used with any of the controllers described herein and variations thereof. As described herein, controller 305 may include a display screen 310 for presenting information, such as healthcare information, to an operator of controller 305. FIG. 4A depicts a screen 405 configured to be displayed on display screen 310 according to some embodiments. As shown in FIG. 4A, screen 405 may include a navigation screen. In some embodiments, navigation screen 405 may include a navigation menu 410 and login graphical user interface (GUI) objects 405 to allow a user to login to the controller 405 and/or a healthcare information software application. Referring to FIG. 4B, therein is depicted a patient navigation screen 405. In some embodiments, a patient navigation screen may include a patient list 420 with various patient information (for instance, a study date, a patient name, a patient identifier, a date of birth, and/or the like). In some embodiments, an operator may select a patient from the patient list 420 to view a patient summary 425 for the selected patient. FIG. 4C depicts an information annotation screen 405 configured according to some embodiments. As shown in FIG. 4C, the annotation screen 405 may include functionality to annotate healthcare information using dictation functions of controller 405 according to some embodiments. In various embodiments, the annotation screen 405 may include a dictation mode screen 430 and an on-screen mode screen 430. FIG. 4D depicts a workflow and configuration screen 405 according to some embodiments. As shown in FIG. 4D, an operator may view a workflow summary screen 440 to view workflow statistics. In addition, an operator may access a screen tools and functions screen 445 to access and modify various settings relating to the controller and/or various aspects of the healthcare information software application, such as image scroll speed and visual settings (for instance, brightness, contrast, and/or the like). In addition to and/or via the controller display screens depicted in FIGS. 4A-4D, display screen 310 may be configured to display RIS, patient lists, risk factors and/or the like to present "low resolution" non-Food and Drug Administration (FDA) monitor information in an easily accessible form factor on controller 305. In this manner, an operator may view such "low resolution" information without having to get up from a workstation or otherwise access such information.

Figure 5A:
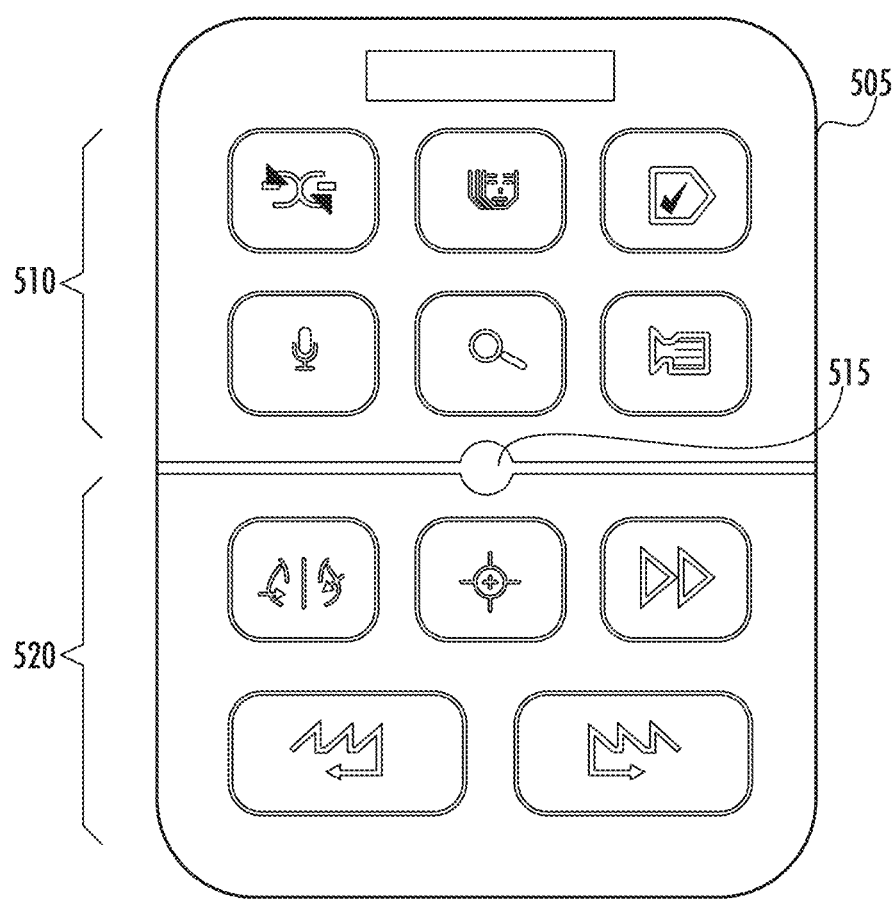

FIGS. 5A-5K depict various aspects of a controller according to a third embodiment. Referring to FIG. 5A, therein is depicted a top-down view of a controller 505 that includes a plurality of programmable buttons 510, a menu toggle 515, and a plurality of default buttons 520. Programmable buttons 510, menu toggle 515, and/or default buttons 520 may have various characteristics according to some embodiments. For example, one or more of programmable buttons 510, menu toggle 515, and/or default buttons 520 may be context-based according to some embodiments. In some embodiments, one or more of programmable buttons 510, menu toggle 515, and/or default buttons 520 may have various physical characteristics, such as being formed of various materials, different sizes, different contours (for instance, concave, convex, and/or the like), different heights (for instance, recessed, raised, and/or level with a surface of controller 305), and/or the like. Embodiments are not limited in this context.

Figure 5B:
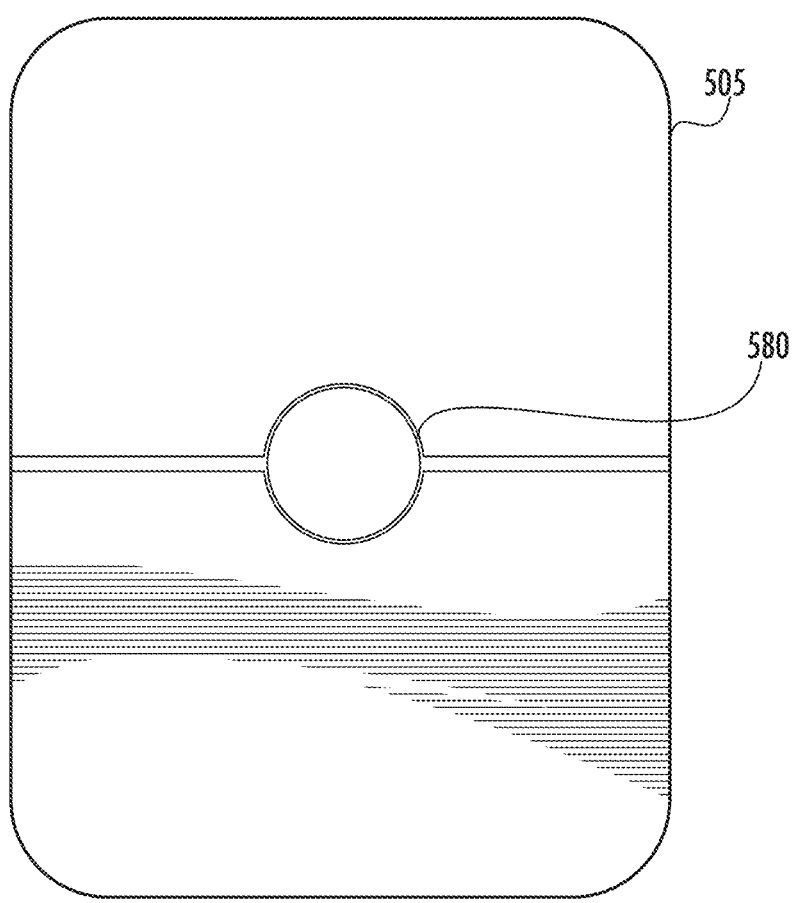

In some embodiments, programmable buttons 510 and/or default buttons 520 may include physical buttons. In some embodiments, menu toggle 515 may allow an operator to scroll through programmable button states, for instance, through sequential actuations. In some embodiments, menu toggle 515 may be actuated from top of controller and/or from either side of controller (see, for example, FIG. 5I). In some embodiments, programmable buttons 510 and/or default buttons 520 may include physical buttons embedded and/or presented via a display. FIG. 5B depicts a back view of controller 505. As shown in FIG. 5B, controller 505 may include an optical sensor 580 configured to detect movement of controller 505 across a surface. In various embodiments, movement of controller 505 as detected by optical sensor 580 may activate various input functions. For example, optical sensor 580 may be configured to allow a radiologist to scroll through images, such as TOMO slices, by moving controller 505 in either of a side-to-side or up-and-down motion.

Figure 5C:
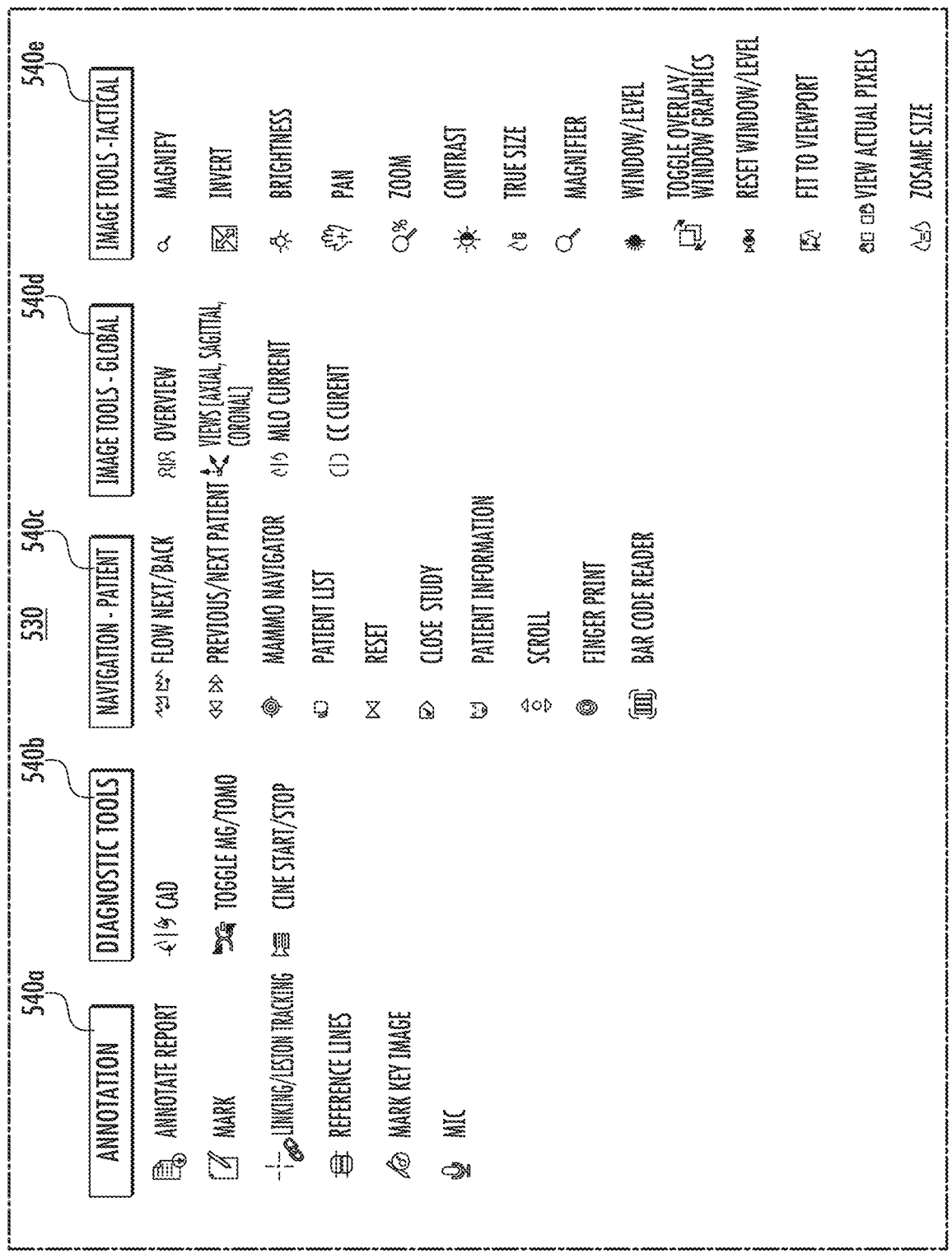
Figure 5D:
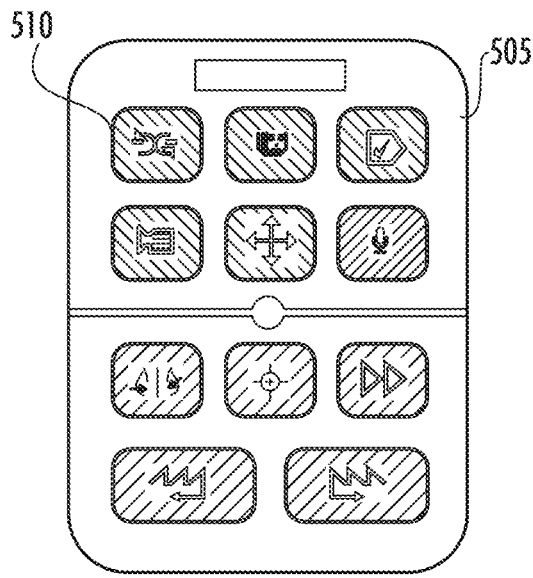
Figure 5E:
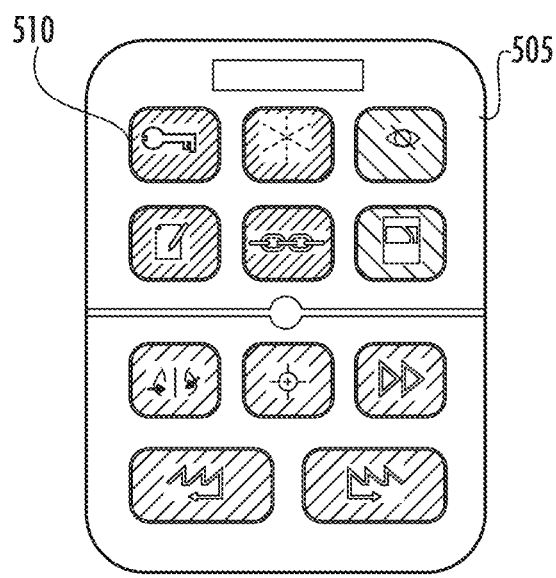
Figure 5F:
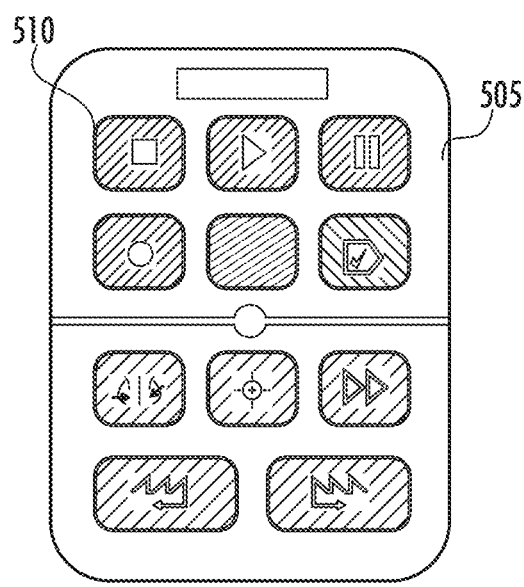
Figure 5G:
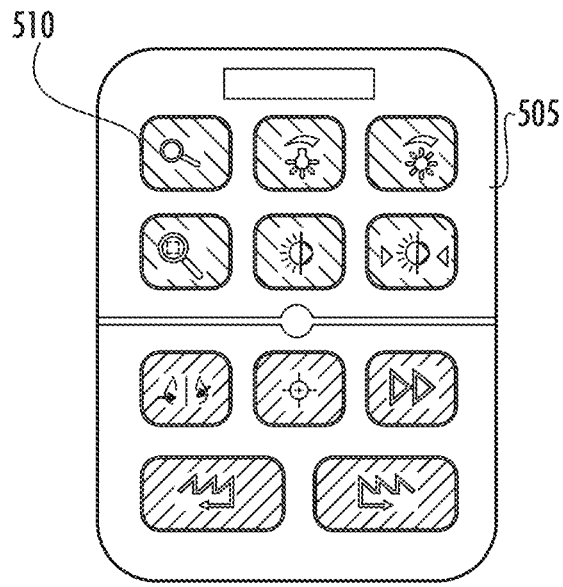

In some embodiments, various control elements of controller 505 may be grouped according to functionality. FIG. 5C depicts functional groupings 530 for controller 505 according to some embodiments. As shown in FIG. 5C, controller may include an annotation functional grouping 540a, a diagnostic tools functional grouping 540b, a navigation-patient functional grouping 540c, an image tools-global functional grouping 540d, and/or an image tools-tactical functional grouping 540e. FIGS. 5D-5G depict controller functional grouping according to some embodiments.

Figure 5H:
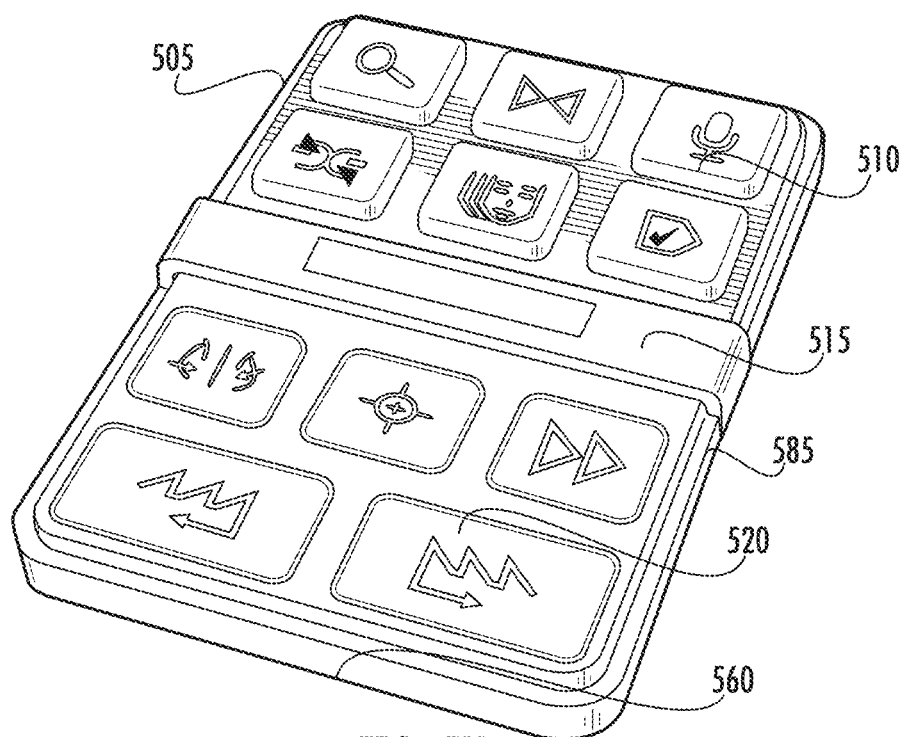
Figure 5I:
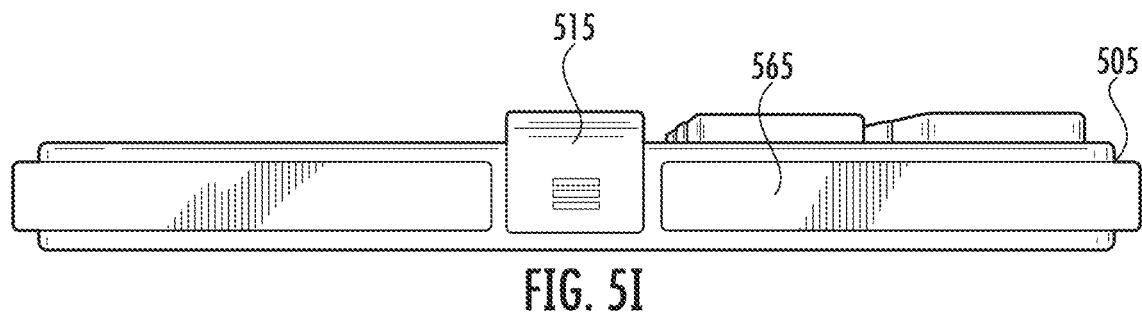
Figure 5J:
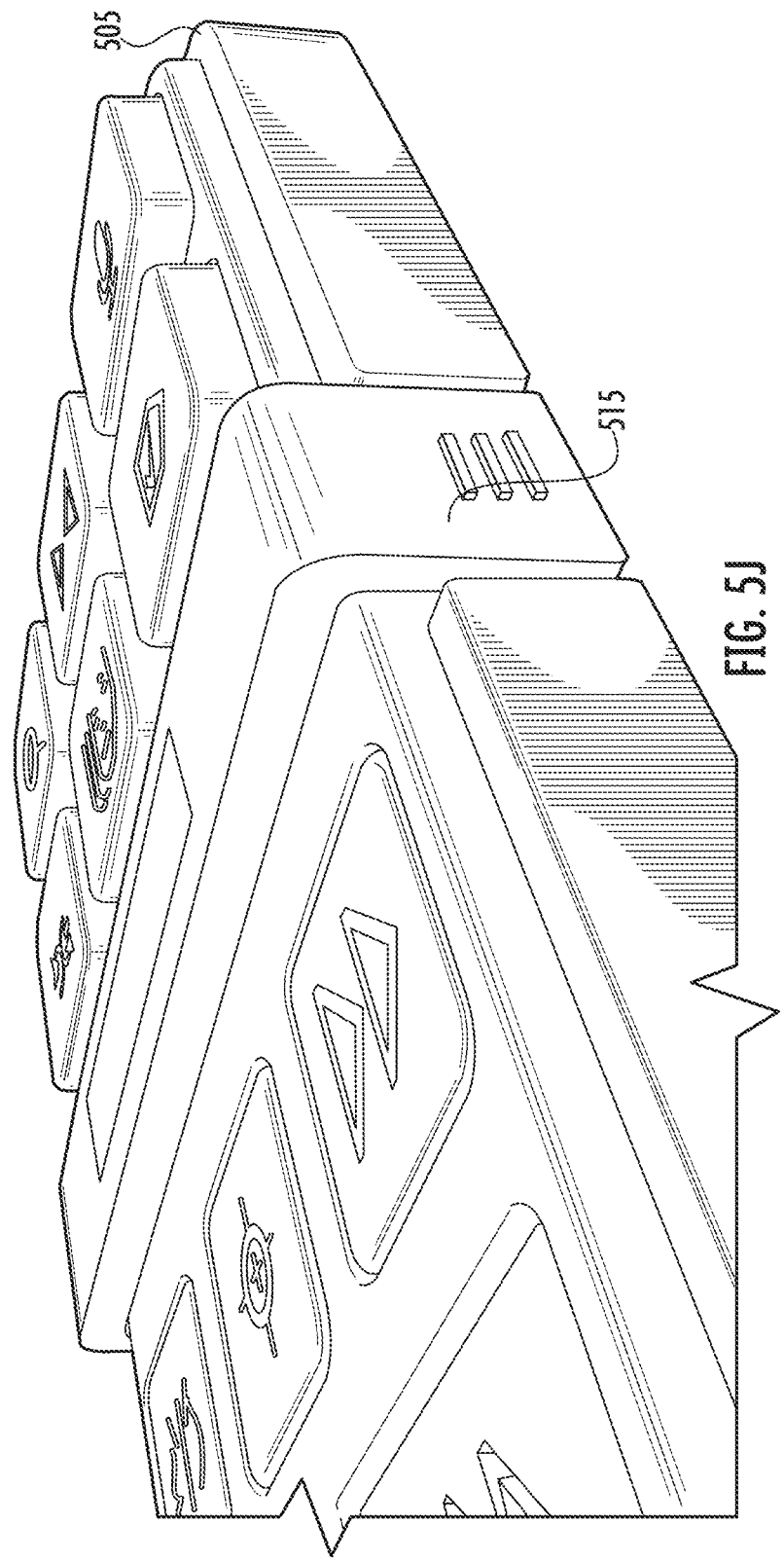

FIG. 5H depicts a top-down view of controller 505 configured according to some embodiments, as depicted in FIG. 5H, controller 505 may include a microphone and speaker. As shown in FIGS. 5H and 5I, menu toggle 515 may have a raised profile in which, for instance, a height of menu toggle may be higher than a height of programmable buttons 510 and/or default buttons 520. Accordingly, in some embodiments, menu toggle 515 may be configured as a palm rest. In an embodiment in which menu toggle 515 is configured as a palm rest, menu toggle 515 may be configured to be actuated via the side of the controller and not the top of menu toggle 515. FIGS. 5I and 5J depict side views of controller 505. In some embodiments, microphone and/or speaker 560 may include a wired/wireless (e.g., Bluetooth®) speaker system to allow for the playing/recording of ambient audio from a third-party device (e.g., a smartphone, PC, and/or the like). In some embodiments, the wired/wireless speaker system may be connected to the dictation system to mute audio while the microphone is active in dictation functions. As shown in FIGS. 5I and 5J, controller 505 may include a wrapped form 565 that facilitates gripping by an operator during scrolling via optical sensor 580. FIG. 5K depicts various variations 570a-f on the form of the controller 505 configured according to the embodiments depicted in FIGS. 5A-5J.

In some embodiments, controller 505 (as well as controllers 205, 305, and 605) may be formed of various materials. In some embodiments, the materials and/or textures thereof used to form controller 505 may be selected, formed, configured, or otherwise arranged to provide contrast between portions of controller 505. In this manner, various elements of controller 505 may serve as physical reference points for a user to be able to discern their hand location on the controller 505 without having to look at controller (for instance, to allow a user to quickly hone in on an element of controller 505). For example, a metal bar 585 surrounding controller 505 may be formed of a material (for instance, a metal material) that has a different texture or feel from the top surface of controller, menu toggle 515, programmable buttons 510, and/or default buttons 520 (for instance, formed of a plastic or rubber (e.g., thermoelastic) material). In some embodiments, a cavity or "moat" may be formed around one or more of programmable buttons 510 and/or default buttons 520. In various embodiments, a physical mark or other protrusion may be formed on menu toggle 515, one or more of programmable buttons 510, and/or default buttons 520. In some embodiments, one or more of programmable buttons 510 and/or default buttons 520 may be have different shapes (for instance, square, round, concave top surface, convex top surface, and/or the like). In some embodiments, a physical reference point may be configured by varying the level of an element with respect to the base surface of controller 505. For instance, menu toggle 515, programmable buttons 510, and/or default buttons 520 may be recessed, raised, level (or "flush"), or otherwise arranged with respect to a base surface of controller. In an example, menu toggle 515 and programmable buttons 510 may be raised (at a same level or a different level with respect to each other) from the base surface of controller 505, while default buttons 520 may be level or recessed with respect to the base surface of controller 505. In some embodiments, buttons associated with a functional grouping 530 may have different characteristics than buttons associated with a different functional grouping 530. Embodiments are not limited in this context. For example, one functional grouping 530 can have a first profile relative to the base portion of the controller 505, while another functional grouping 530 may have a second profile relative to the base portion of the controller 505, in which the first profile is different than the second profile. Although the varying characteristics have been described with respect to controller 505, embodiments are not so limited, as the elements of any of controllers 205, 305, and 605 may be configured to have varying physical characteristics as described with respect to controller 505.

Figure 6A:
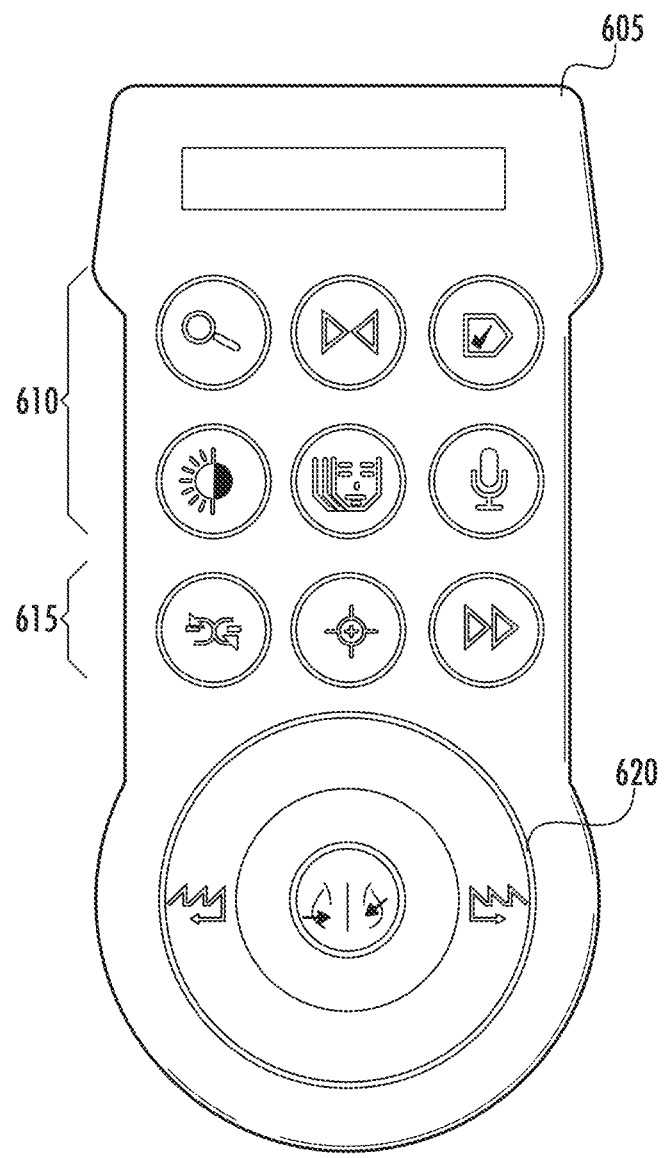
FIGS. 6A-6K depict various aspects of a controller according to a fourth embodiment.
Figure 6B:
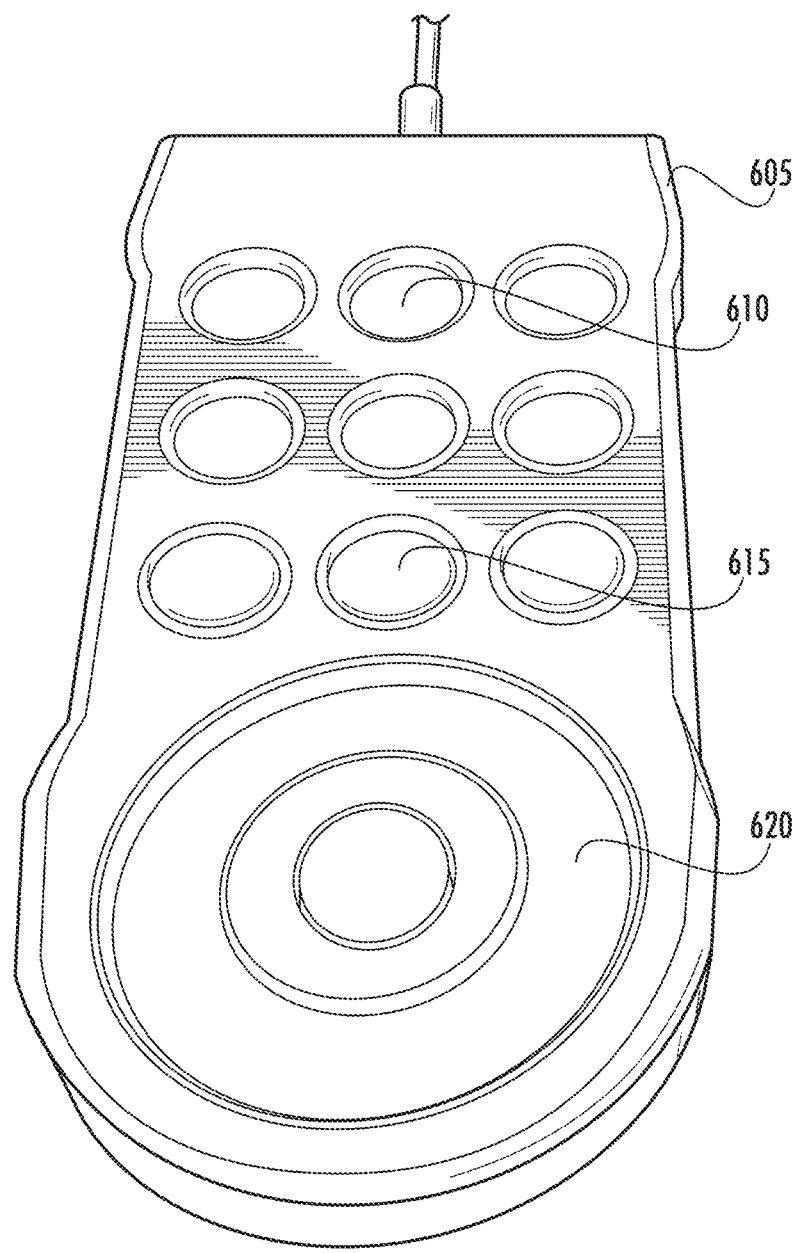
Figure 6C:
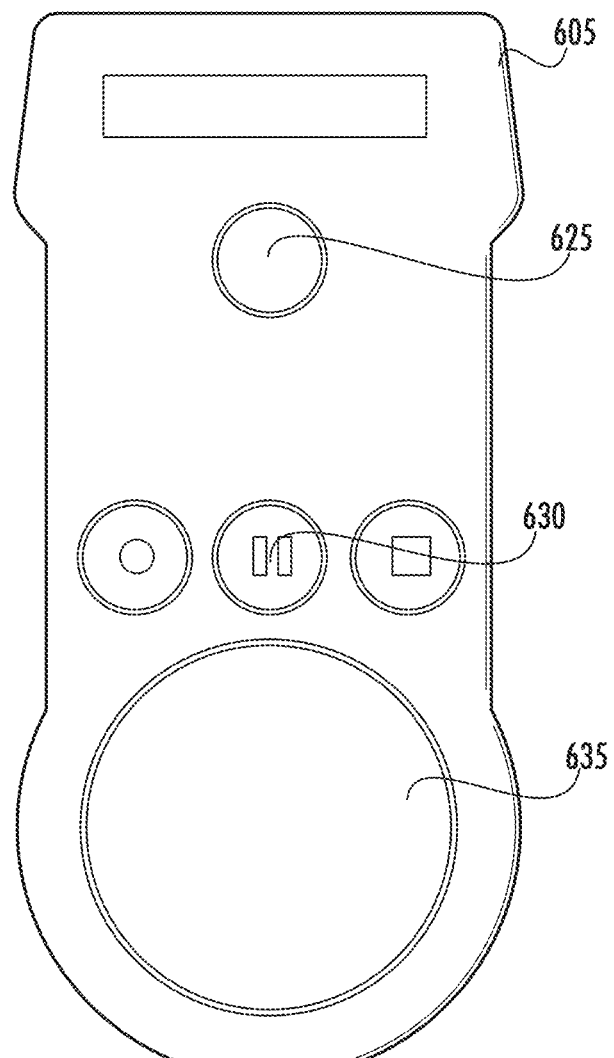
Figure 6D:
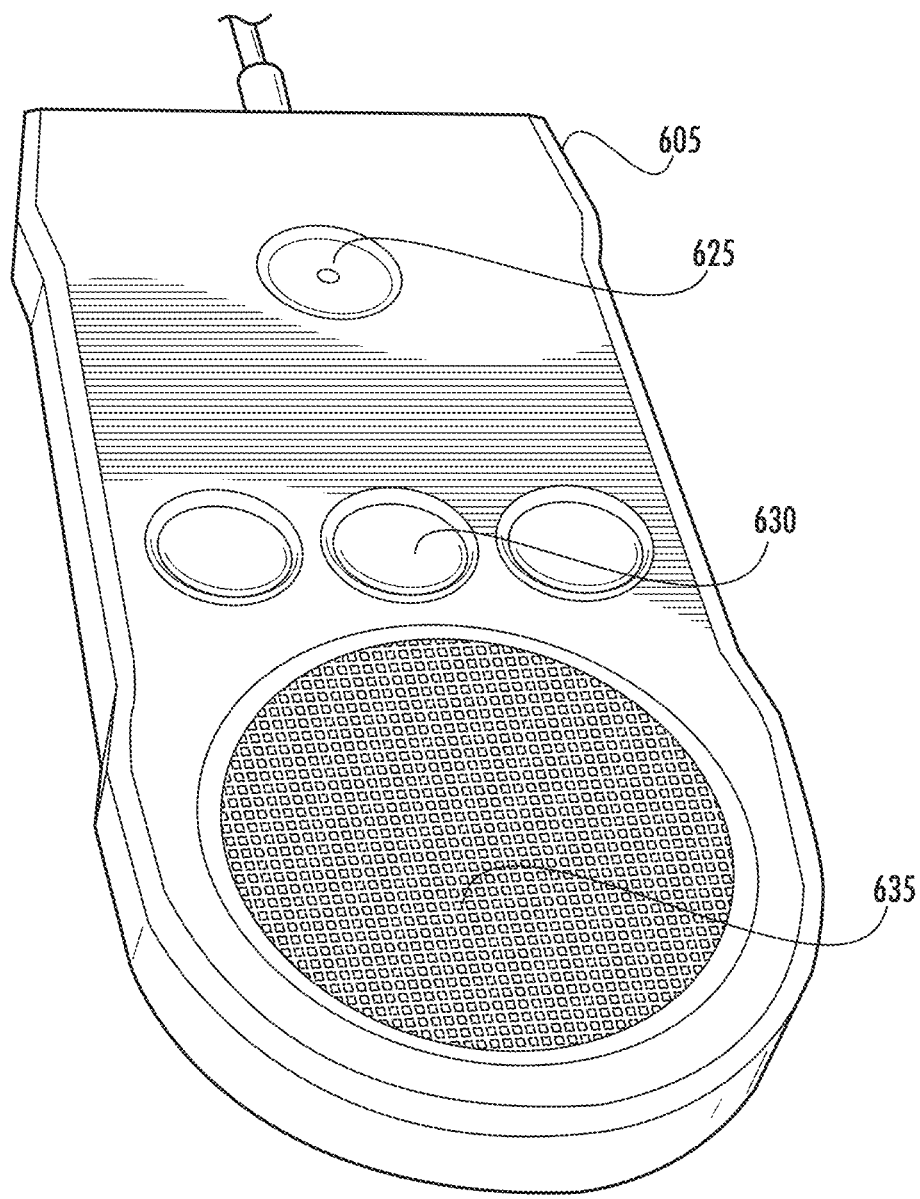

FIGS. 6A-6K depict various aspects of a controller according to a fourth embodiment. Referring to FIGS. 6A and 6B, therein is depicted a top-down view of a controller 605 that includes a plurality of programmable buttons 610, a plurality of default buttons 615, and a scroll wheel 620. FIGS. 6B and 6C depict a bottom view of controller 605. As shown in FIGS. 6B and 6C, controller 605 may include an optical sensor 625 for optical scroll input, dictation controls 630, and a speaker 635 on a bottom side of controller 605. In some embodiments, controller 605 (as well as controllers 205, 305, and 505) support multi-modal digital image reading by facilitating use of tools for US, MRI, TOMO, and/or the like in a single controller.

Figure 6E:
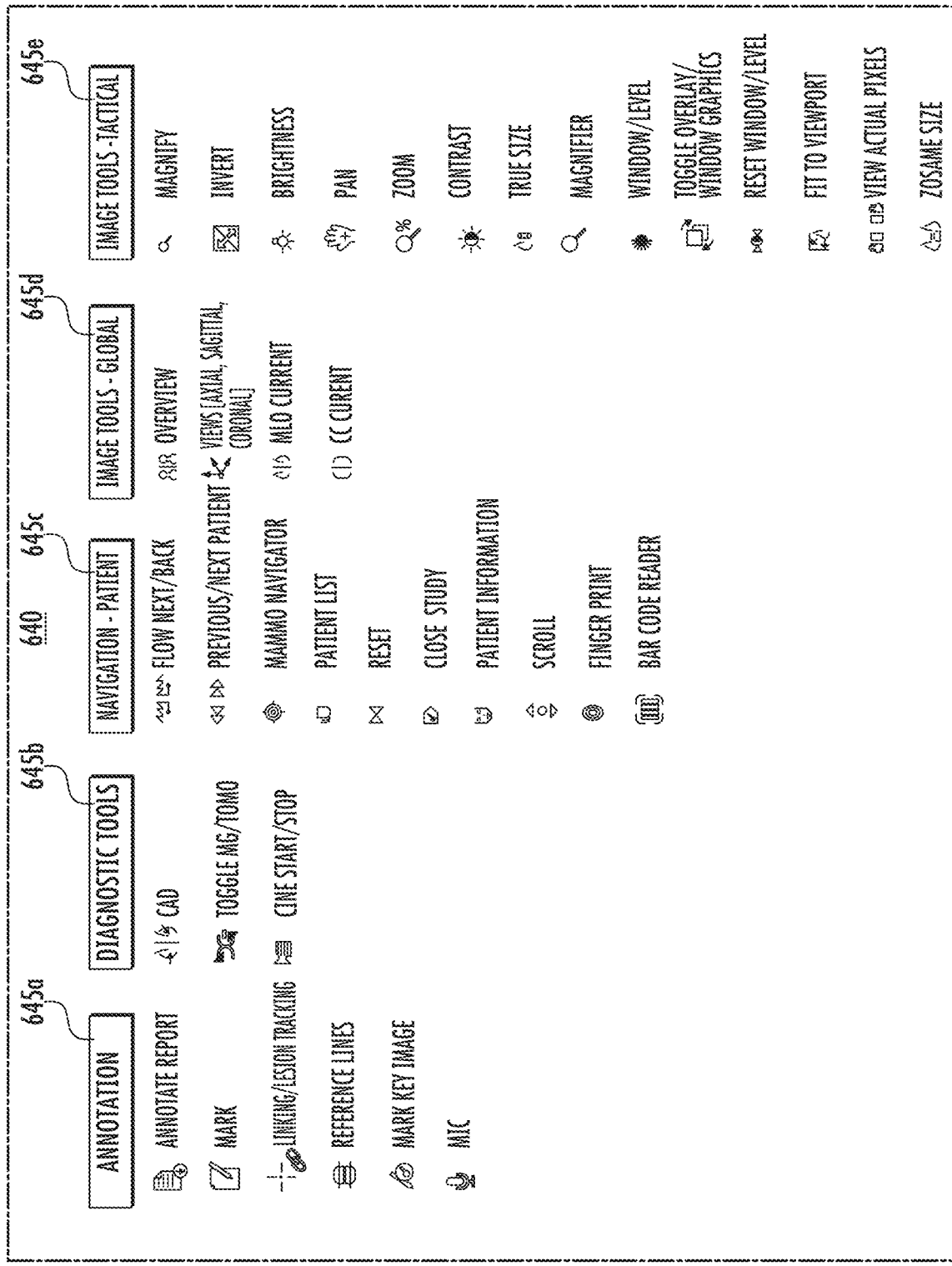
Figure 6F:
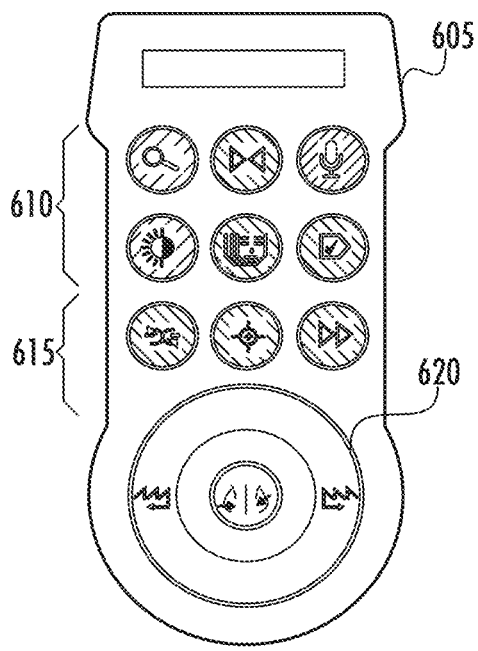
Figure 6G:
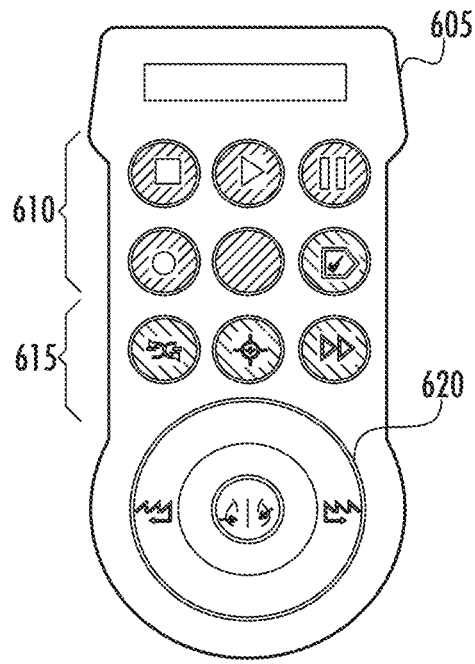
Figure 6H:
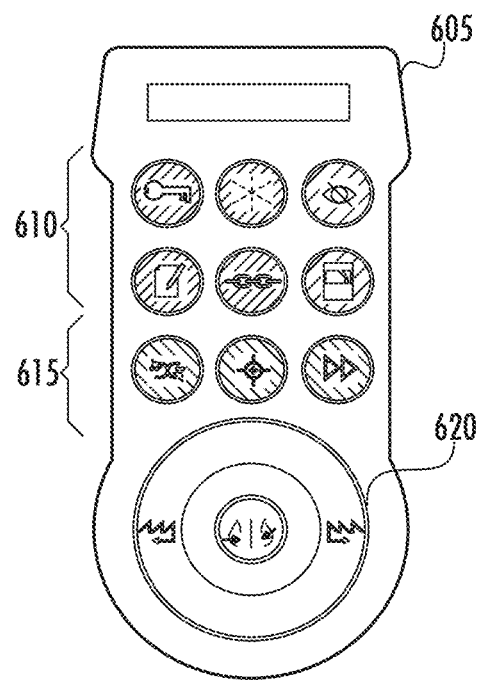
Figure 6I:
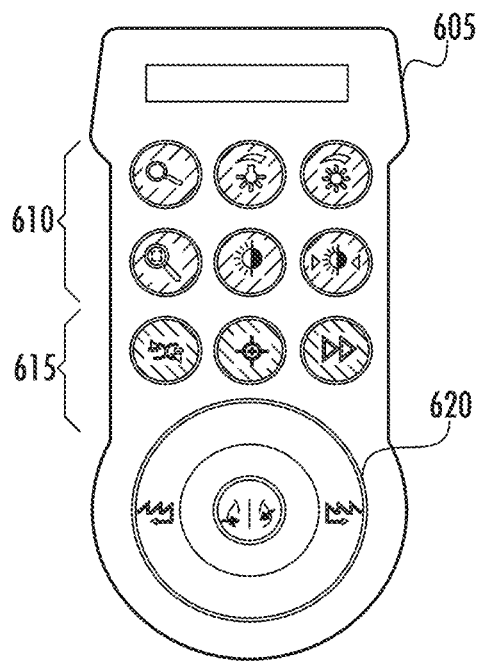
Figure 6J:
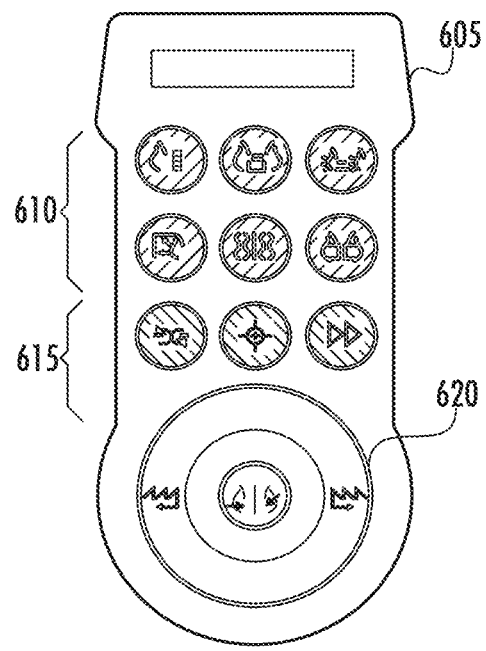
Figure 6K:
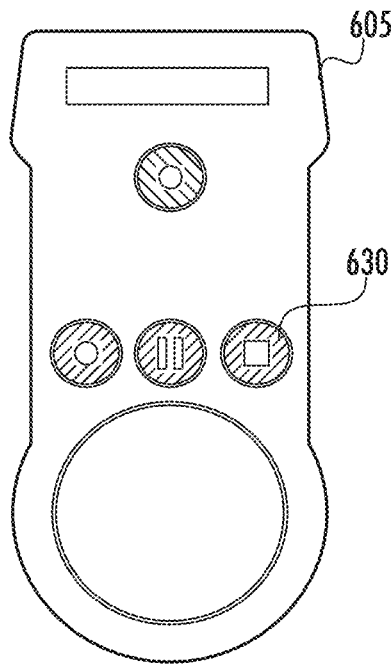

In some embodiments, various control elements of controller 605 may be grouped according to functionality. FIG. 6E depicts functional groupings 640 for controller 605 according to some embodiments. As shown in FIG. 6E, controller may include an annotation functional grouping 645a, a diagnostic tools functional grouping 645b, a navigation-patient functional grouping 645c, an image tools-global functional grouping 645d, and/or an image tools-tactical functional grouping 645e. FIGS. 6F-6K depict controller functional grouping according to some embodiments.

Figure 7A:
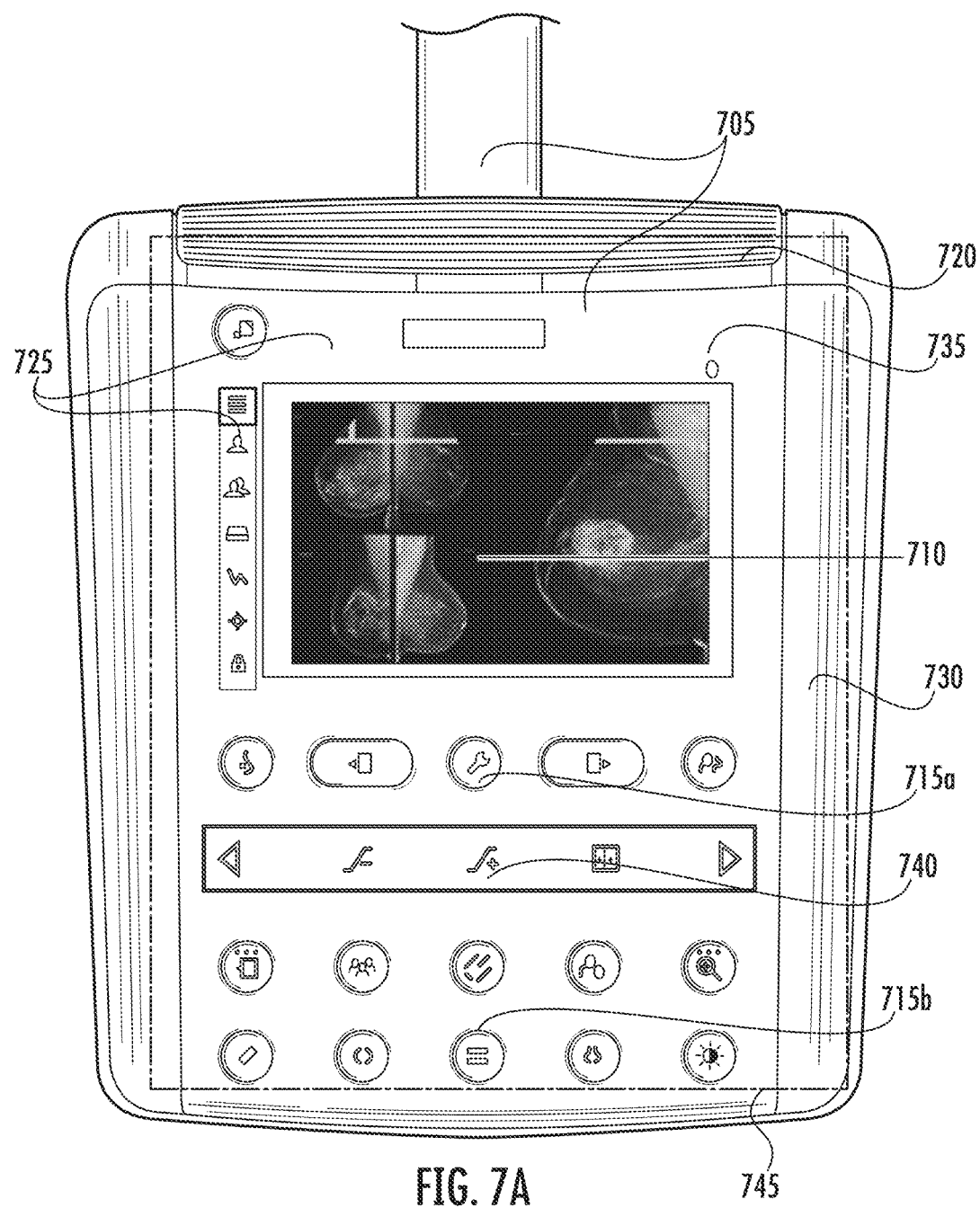
FIGS. 7A-7L depict various aspects of a controller according to a fifth embodiment.

FIGS. 7A-7L depict various aspects of a controller according to a fifth embodiment. Referring to FIG. 7A, therein is depicted a controller 705 that includes a plurality of touch button controls 715, a scroll wheel 720, and a display screen 710. Although controller 705 may include a plurality of touch button controls 715a and 715b, only the two sets are labeled to simplify the figures. In some embodiments, scroll wheel 720 includes a physical scroll wheel as further shown and described in FIG. 7C. The display 710 may include a multi-touch color display which may be a LCD touch screen and extends centrally to the controller 705 surrounded by rest areas 730.

The controller 705 together with display screen 710 may be used as an extension of the display 130 of the workstation 120. Such display extension allows keeping the radiologists in the reading zone and focused on the images displayed on the workstation 120 rather than be distracted with moving to a different location. In addition, the display screen on the workstation 120 is a high resolution high pixel count display that is custom for viewing diagnostic and screening x-ray and other modalities and is FDA approved. By utilizing the display screen 710 for functions that are lower resolution, such as image overview (i.e. "MammaNavigator") and annotation tools, reduces the overall cost of the workstation 120 and the need to provide additional expensive diagnostic screens 130.

In some embodiments, display screen 710 may be configured to provide an embedded graphic display to aid in annotation and to provide an additional display for viewing third-party related healthcare information (e.g., RIS and notation software), without requiring an operator to physically move to a different location to view for example patient records or history. In addition, secondary screens used for patient information (see, for example, FIGS. 4A-4D) may enhance operator workflow when used with multiple palettes, when switching between applications, for reference or comparison, and/or the like. In some embodiments, the display 710 may be used for annotation right in the image using the touch-control features. For example, the radiologist may view a mammography image on the display 710 and may use the touch features to mark or highlight a portion of the image indicating a suspicious region and add a notation indicating follow up images or procedures. In other embodiments, the display screen 710 may display different modalities than the modality displayed on the workstation display 130. For example, the display 130 of the workstation 120 may be used to display images associated with one modality (i.e. mammography), while display screen 710 may display images associated with another modality (i.e. ultrasound or MRI). In another embodiment, the display 130 is used to display one image view, for example, the left CC-view, while the display screen 710 can be used to display another image view, for example, left MLO view. In another embodiment, the display 710 can be used to view the overview of the patient's images (i.e. "MammoNavigator"). It is appreciated that such extended viewing on the display 710 improves the radiologist's workflow as this allows using one image or healthcare information as a reference image on the display 710 while reviewing additional images on the workstation 120.

In some embodiments, the display 710 may include toggle display controls 725. The toggle display controls 725, similar to the adaptive display controls 740 (further described below) are context based and dynamic. In other embodiments, the toggle display controls 725 can allow the user to toggle through a number of functions and options. For example, the controller 705 may receive a toggle command from the user via the display screen 710, and display a first set of toggle display controls 725. The controller 705 can receive another toggle command and display a second set of toggle display controls 725. In one example, the first set of toggle controls may include image manipulation tools such as the tools 250a described with reference to FIG. 2K, and the second set of toggle controls may include annotation tools such as tools 250c. The user may toggle between image manipulation and annotation tools allowing different functionality to be used on the same display screen 710. This allows minimization of visible controls to be blocking the radiologist reviewing screen. It is appreciated by the inventors that maximizing the reviewing screen provides for a minimal amount of on-screen distraction from reviewing the images.

In various embodiments, the display screen 710 may be additionally be used for navigation control of the workstation 120. For example, a user may toggle this feature on or off, when toggled on, the display screen 710 functions as a pointing device that detects two-dimensional motion of a user's finger relative to the surface of the display. The motion of the finger can be translated into the motion of a pointer on the workstation display 120, further allowing smooth control of the graphical user interface on the display 120 (similar to a track pad on a computer laptop). Inventors have appreciated that such functionality allows the user to eliminate the use of an extra pointing device which would be typically associated with each of the workstations and displays when multiple workstations and displays are used. This allows the user to increase workspace on the desktop and reduce confusion since multiple pointing devices may be used with multiple workstations.

Figure 7B:
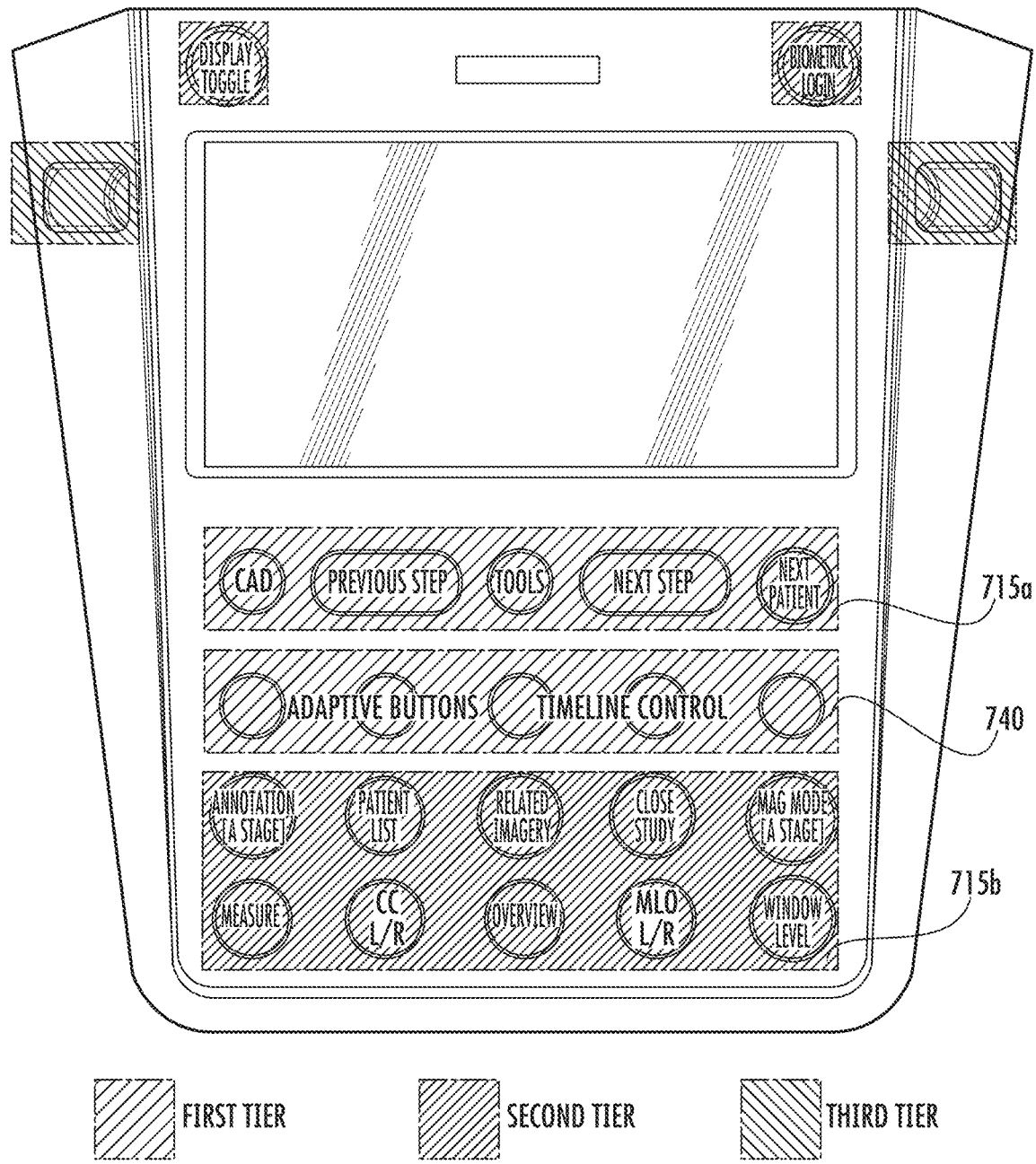

In various embodiments, a portion of the display screen 710 includes the adaptive display controls 740 may be context-based according to some embodiments, for example as described above with reference to FIGS. 2A and 2K and additionally shown in FIG. 7B. In various embodiments, the relevant context for context-based adaptive display controls 740 may be based on the image modality being displayed, the functionality being presented, or information presented via display screen 710, and/or combinations thereof.

In one embodiment, the adaptive display controls 740 may display a symbol of the function it performs. The user may redefine the function of the adaptive display controls 740 and the symbol associated with the reprogrammed function may appear to indicate the new function of the adaptive display controls 740. In some embodiments, the customizations and preferences are shared between hardware controller and software displayed on the workstation 120. For example, the user may define a function on the software displayed on the workstation and the same function is displayed on the controller 205.

In addition to the context-adaptive display functionality, the adaptive display controls 740 can function as a horizontal scroll wheel. For example, the entire section of the adaptive display controls 740 can be used and be configured to accept an input from the user who moves his finger from one side of the adaptive display controls section to the other. Such horizontal scroll, in one example can be used to view a timeline progression of images, such as images taken at different time points, or even different images taken at the same time. The adaptive display controls 740 can receive the scroll input at different speeds and the controller 705 can correlate the different speed of movement to different scroll speed. It is appreciated by the inventors that such horizontal scrolling motion is more intuitive for scrolling functions that associated with scrolling through images taken at different times. In turn the physical scroll wheel is rotated in the vertical direction and such a motion is more intuitive for scrolling through tomography images.

In some embodiments, one or more of touch button controls 715a and 715b may have various physical characteristics, such as being formed of various materials, different sizes, different contours (for instance, concave, convex, and/or the like), different heights (for instance, recessed, raised, and/or level with a surface of controller 705), and/or the like. For instance, as shown in FI. 7B, the touch button controls 715a may include first tier functions which are more frequently or universally used. The touch button controls 715a may be raised above the surface of the controller 705. The touch button controls 715b may include second tier functions and the buttons may be recessed below the surface of the controller 705. This allows for the palm of the user when resting on the rest area 730 to not accidently activate the buttons with the palm of the hand. As described above with reference to FIG. 2B, the buttons may be square, round or may further include grouping features on the surface of the controller 705, such as groove encircling the buttons 715a and 715b.

In general, areas of controller 705 configured as "rest areas" (for instance, palm rest area 745) may be configured around functional interfaces (for instance, touch button controls 715a and 715b and the display 710) while allowing a portion of a hand to rest without activated a function. The surfaces designated as rest areas are intended to be approach zones and active palm/hand rests devoid of sharp edges. In the example shown in FIG. 7A, the rest areas 730 extend in a horse-shoe fashion around the perimeter of the display 710, starting from the scroll edge 708, vertically across the length of the controller 705, horizontally along the bottom of the controller 705 and vertically across the length of the controller 705, ending at the edge 706 as indicated by the dashed line 745. Embodiments are not limited in this context.

Figure 7C:
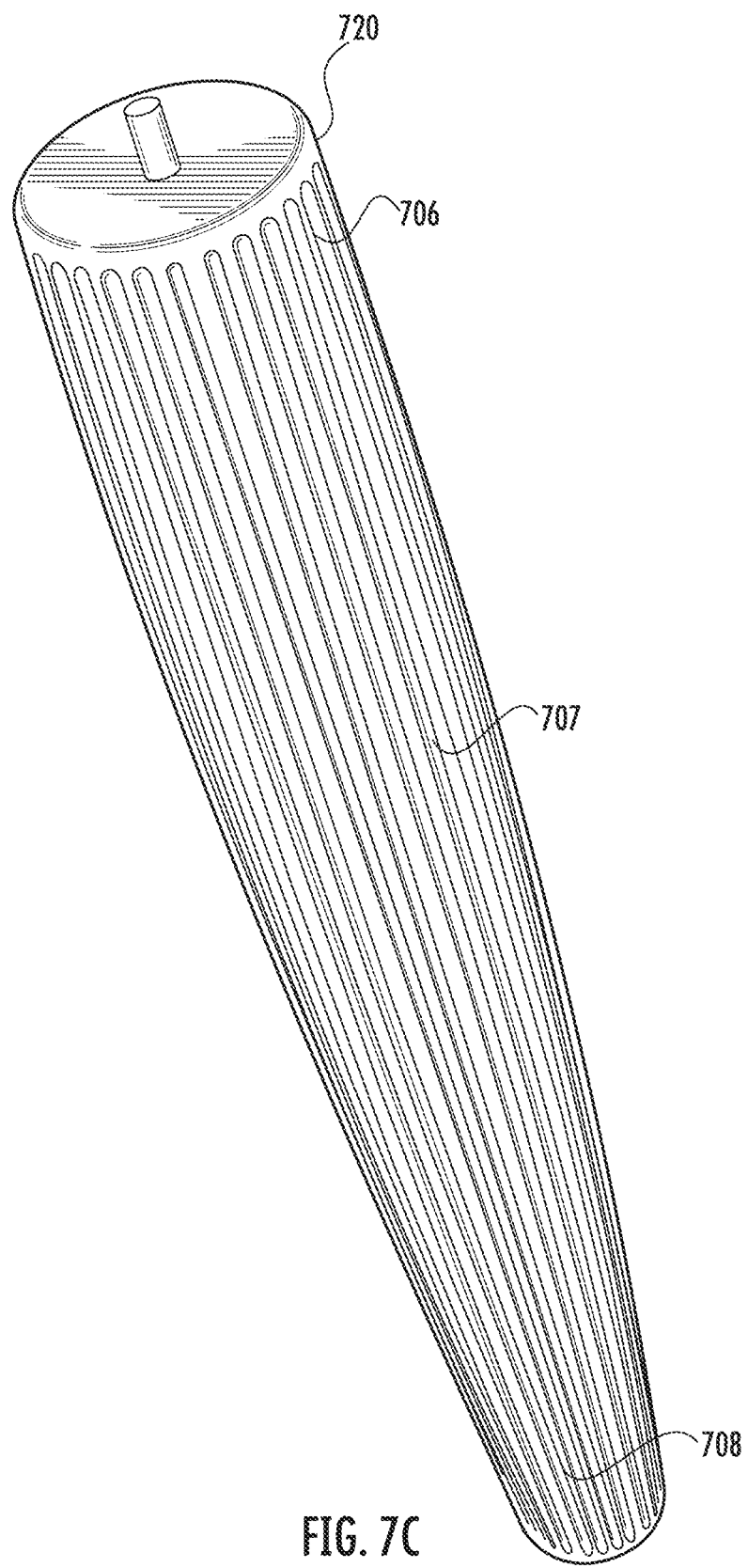
Figure 7D:
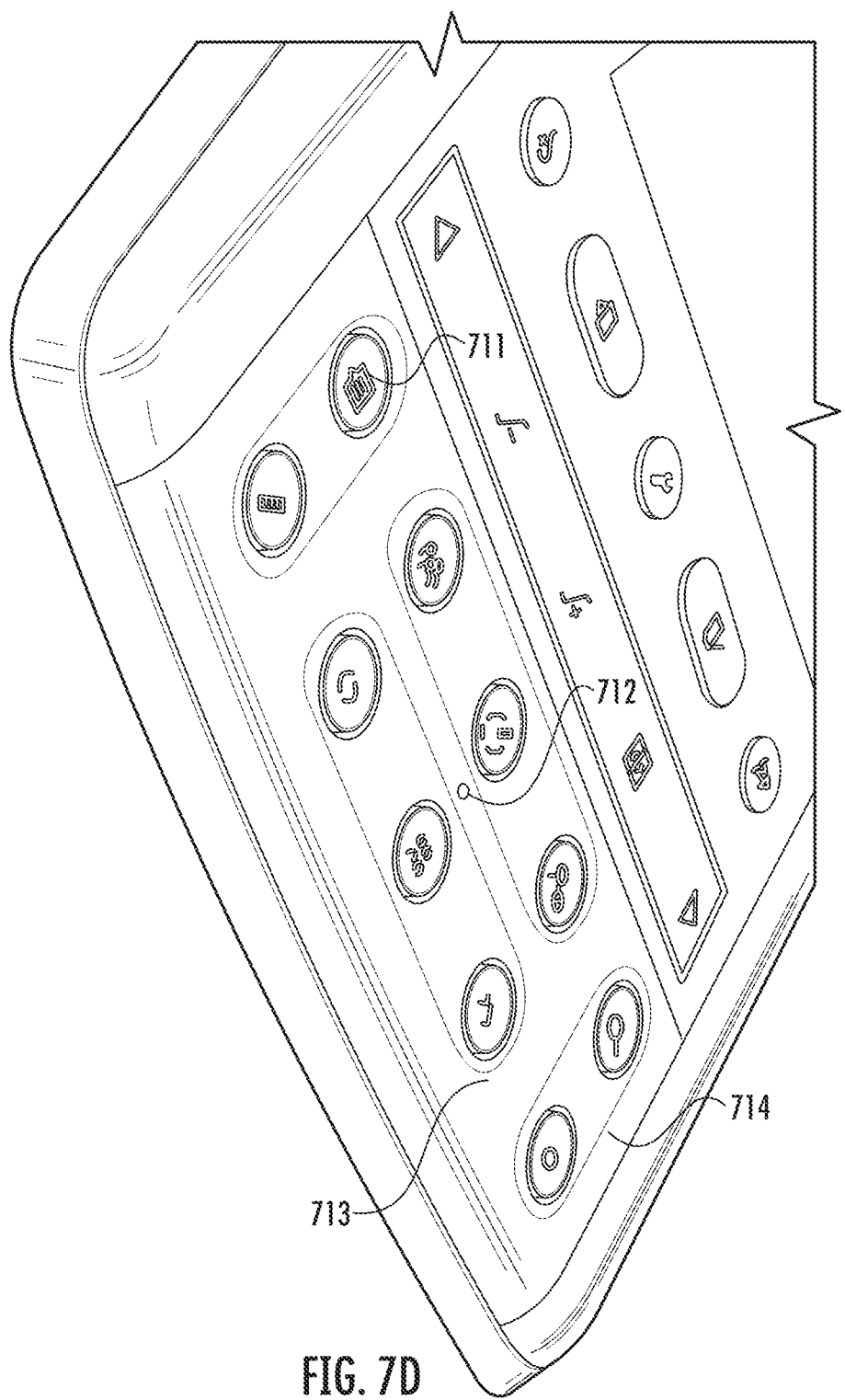
Figure 7E:
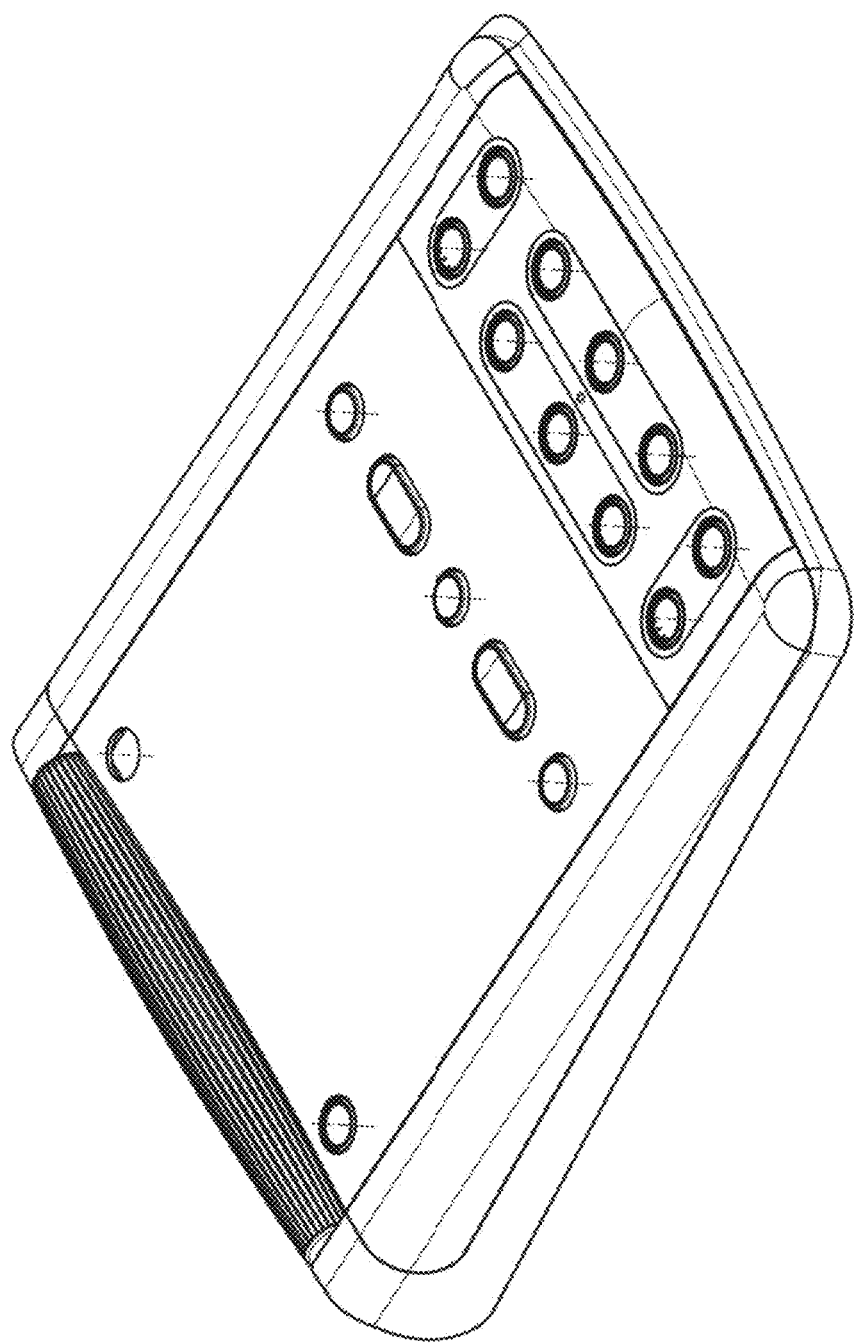
Figure 7F:
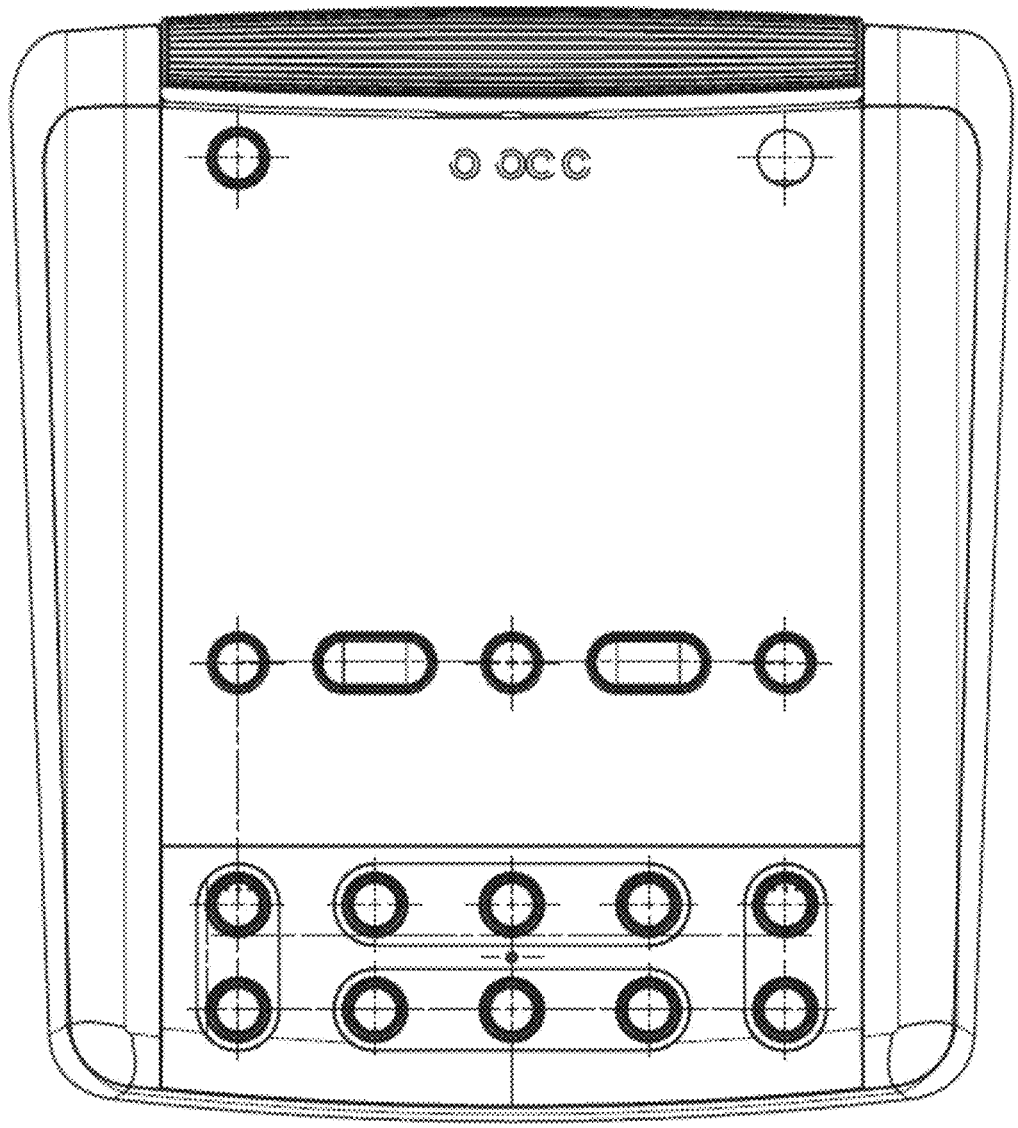
Figure 7G:
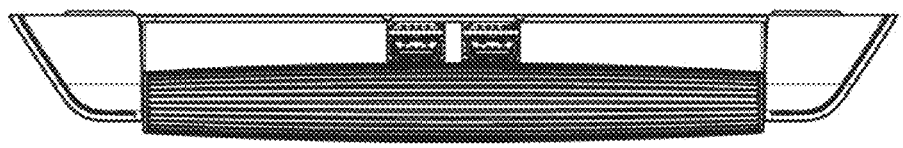
Figure 7H:
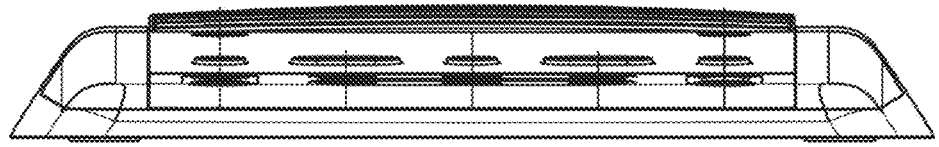
Figure 7I:
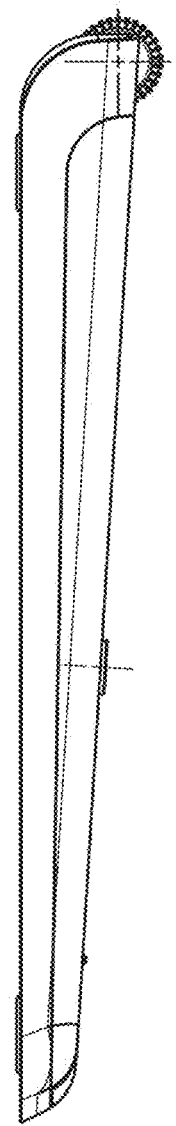
Figure 7J:
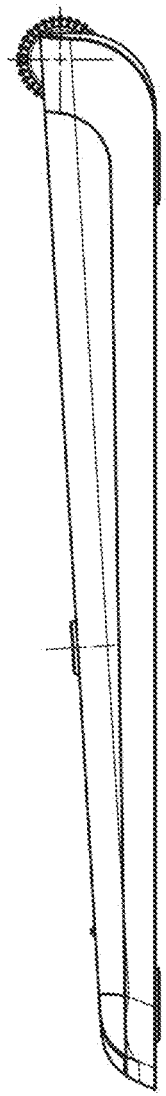
Figure 7K:
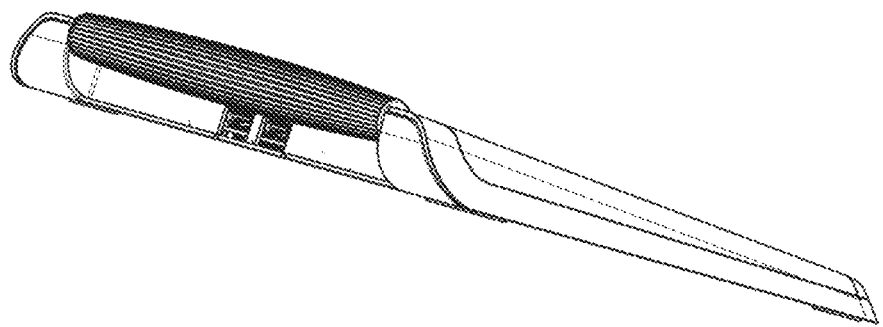
Figure 7L:
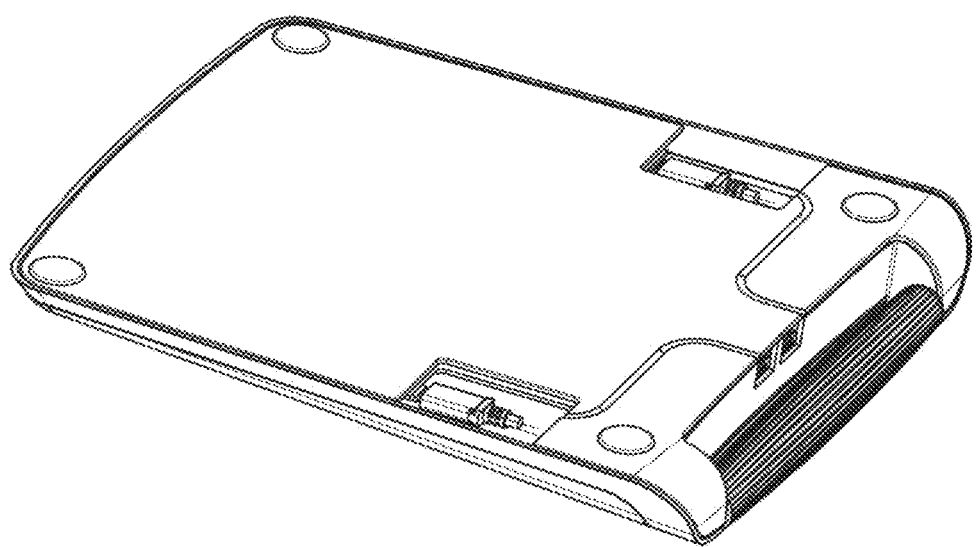

In various embodiments, the controller 705 may include physical homing features as shown in FIG. 7D. The homing features include physical characteristics that allow the user to identify the placement of the user's hand on the controller 705 without looking down to it. The homing features 711, 712, 713, 714 are showed, but embodiments are not limited in this context. Homing feature 711 includes three raised dots on one of the touch control button 715b. A user's hand touching the raised dots would know, along with other physical indicators, such as the proximity to the edge of the controller 705 that the user's hand is located at the lower left corner of the device. Homing feature 712 is a single raised dot at the center of the controller 705 and indicates the central location of the user's hand. Homing features 713 and 714 are grooves encircling and grouping the touch-control buttons 715*b* as described above. A vertical grouping such as 714, indicate one functionality, while a horizontal grouping such as 713 indicates another functionality. These and other homing features within the scope of this application allow to minimize the amount of distraction for the user and allows them to perform the task on "auto-pilot," overtime building physical memory of certain tasks and functions.

Some of the touch control buttons 715*b*, may include multi-functional operation, such as for example touch control button 715*b* shown in FIG. 7D having the three raised dots homing feature. One example of multi-function control includes sequential button control. The sequential button control allows for a greater amount of functionality to be included in the controller 705 while minimizing the footprint or size of the controller. In one example, the sequential button control can have two of more functions that can be accessed by toggling or pressing the sequential button. For example, the sequential button may be pressed one to access a first functionality, the sequential button is then pressed again to access a second functionality, and pressed again to return to the first functionality. Any number of functions programmed into the sequential button control are contemplated. In another example, haptic button control may be used to send vibrational feedback to the user to indicate activation of a first function or a second function in a multi-function operation.

In some embodiment, the scroll wheel 720, as shown in FIG. 7C, includes a tapered design having two edges 706 and 708 and a central section 707 that allow for modulating scroll speeds. The width of the ends 706 and 708 comprise a smaller diameter than the central section 707 creating variable input ratios. The taper from the edges 706 and 708 to the central section 707 is gradual, allowing variable input ratios to gradually change from the edges to the center. The radiologist may touch the smaller diameter edges 706 and 708 either left or right handed to access the scrolling function. To scroll faster the radiologist can use the smaller diameter outboard edges of the scroll wheel and the central larger diameter section of the scroll wheel 720 to scroll slower. The scroll wheel 720 include grooves having a length from edge 706 to edge 708. The number of grooves surrounds the circumference of the scroll wheel 720 and allow for easy control of the scroll wheel by the user. In one example implementation the scroll wheel can be used to scroll through Tomography ("Tomo") images having a number of images or slices (for example 15 images) taken at different degree angles of the rotating x-ray source and detector. A radiologist may prefer to scroll quickly through all the Tomo images to get an overview of the patient, then scroll slowly while reviewing images deemed to be of particular interest or those showing signs of suspicious cancerous regions.

FIG. 7E-7L show additional views of the controller 705.

Figure 8:
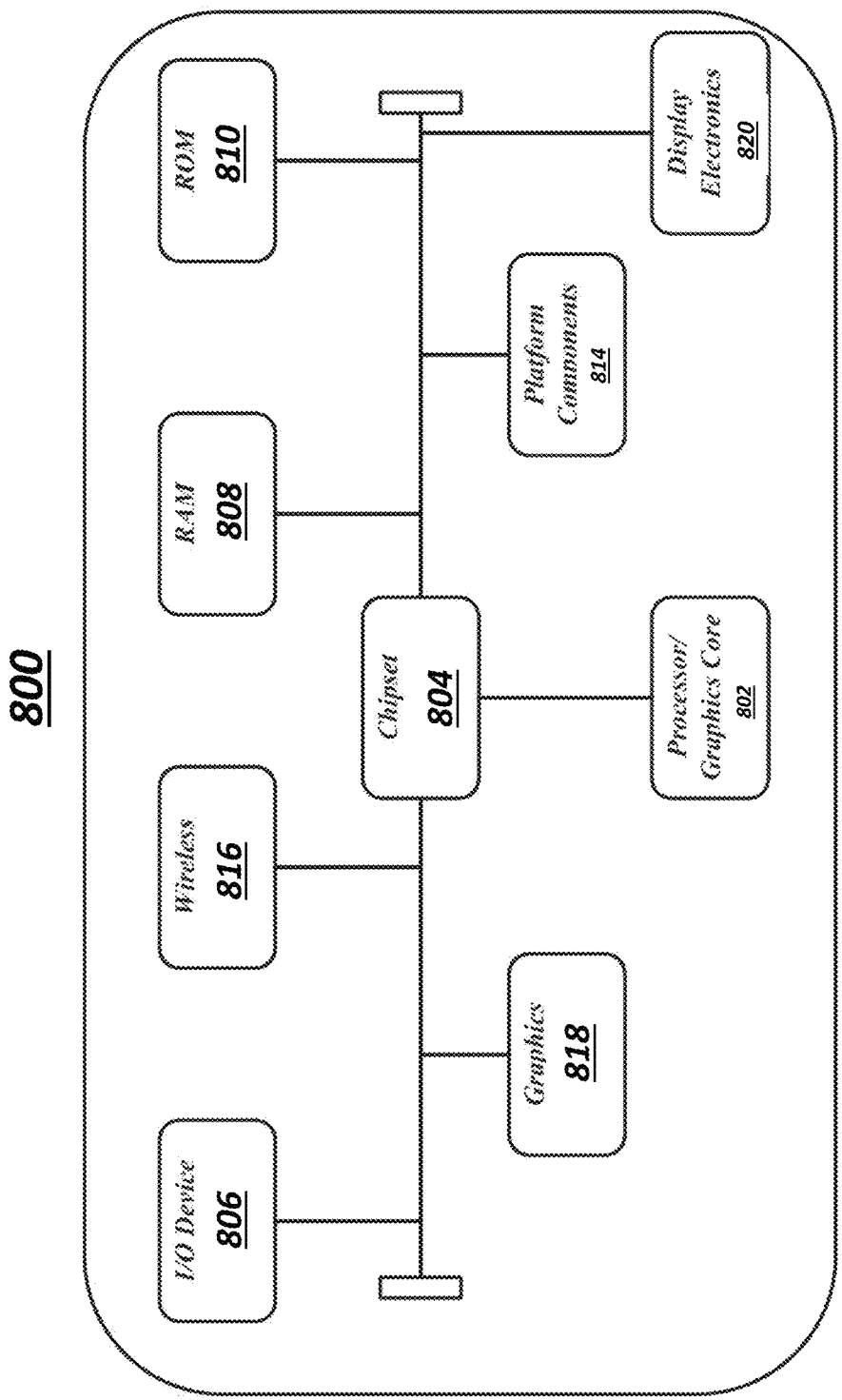
FIG. 8 depicts various aspects of a controller according to a fourth embodiment.

FIG. 8 depicts an illustrative device according to an embodiment. More specifically, FIG. 8 is a diagram of an exemplary system embodiment and in particular, depicts a platform 800, which may include various elements. For instance, this figure depicts that platform (system) 800 may include a processor/graphics core 802, a chipset/platform control hub (PCH) 804, an input/output (I/O) device 806, a random access memory (RAM) (such as dynamic RAM (DRAM)) 808, and a read only memory (ROM) 810, display electronics 820, and various other platform components 814 (e.g., a fan, a cross flow blower, a heat sink, DTM system, cooling system, housing, vents, and/or the like). System 800 may also include wireless communications chip 816 and graphics device 818. The embodiments, however, are not limited to these elements.

As depicted, I/O device 806, RAM 808, and ROM 810 are coupled to processor 802 by way of chipset 804. Chipset 804 may be coupled to processor 802 by a bus 812. Accordingly, bus 812 may include multiple lines.

Processor 802 may be a central processing unit comprising one or more processor cores and may include any number of processors having any number of processor cores. The processor 802 may include any type of processing unit, such as, for example, CPU, multi-processing unit, a reduced instruction set computer (RISC), a processor that have a pipeline, a complex instruction set computer (CISC), digital signal processor (DSP), and so forth. In some embodiments, processor 802 may be multiple separate processors located on separate integrated circuit chips. In some embodiments processor 802 may be a processor having integrated graphics, while in other embodiments processor 802 may be a graphics core or cores.

Some embodiments of the disclosed device may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A controller comprising:
   a context-adaptive button comprising a physical button with dynamic functionality for manipulating, editing, or annotating digital medical images on a display;
   the controller configured to:
   determine a first context of the digital medical images;
   associate the context-adaptive button with a first function for manipulating, editing, or annotating the digital medical images;
   after associating the context-adaptive button with the first function, determine a second context of the digital medical images;
   in response to determining the second context, associate the context-adaptive button with a second function for manipulating, editing, or annotating the digital medical images;
   after associating the context-adaptive button with the second function, determine a user examination of a section of one image of the digital medical images;
   in response to determining the user examination of one image of the digital medical images, associate the context-adaptive button with a third function for manipulating, editing, or annotating the digital medical images, wherein the second function is different than the third function; and
   receive a toggle command from the display to switch between a first toggle function for manipulating, editing, or annotating the digital medical images and a second toggle function for manipulating, editing, or annotating the digital medical images, wherein the first toggle function and the second toggle function are different.

2. The controller of claim 1, wherein the at least one of the first context and the second context comprises at least one of a dictation mode, patient information associated with the digital medical images, a controller setting, image overview, workflow information, breast tomosynthesis viewing mode, breast 2D mammography viewing mode, breast magnetic resonance viewing mode, breast ultrasound viewing mode, and computed tomography viewing mode.

3. The controller of claim 1, wherein determining the at least one of the first context and the second context comprises receiving information from a computing device connected to the controller.

4. The controller of claim 1, wherein the first function comprises one of:
   an annotation tool;
   a patient workflow tool;
   a global image tool;
   a navigation tool; or
   a tactical image tool.

5. The controller of claim 1, the digital medical images comprising at least one of:
   a breast tomosynthesis image;
   a breast 2D mammography image;
   a breast magnetic resonance image;
   a breast ultrasound image; and
   a computed tomography image.

6. The controller of claim 1, wherein the controller is configured to:
   in response to determining the at least one context, display an indication of the second function on the display screen of the controller.

7. The controller of claim 1, the display screen comprising a touch screen.

8. The controller of claim 1, wherein the context-adaptive button is programmable.

9. The controller of claim 1, wherein the controller further comprises a plurality of embedded controls.

10. The controller of claim 1, the controller further comprising a scroll wheel comprising a variable diameter.

11. The controller of claim 10, wherein the variable diameter is configured to control the speed of scrolling through slices of constructed breast tomosynthesis images.

12. The controller of claim 10, wherein the digital medical image is a constructed breast tomosynthesis image, and wherein the controller is configured to:
   based on an activation of the scroll wheel, cause a scroll action through slices of the constructed breast tomosynthesis image on a display of a computing device.

13. The controller of claim 10, wherein the controller is configured to cause scrolling of at least one of the digital medical images at a first speed based on activation of the scroll wheel in a first position with a first diameter, and cause scrolling at a second speed based on activation of the scroll wheel in a second position with a second diameter.

14. The controller of claim 1, wherein the controller comprises a plurality of buttons arranged in a functional grouping, the plurality of buttons including the context-adaptive button.

15. A method of manipulating healthcare information, comprising:
   receiving user input associated with digital medical images at a controller, the controller comprising a context-adaptive button comprising a physical button with dynamic functionality for manipulating, editing, or annotating the digital medical images on a display;
   the controller configured to:
   determine a first context of the digital images;
   associate the context-adaptive button with a first function for manipulating, editing, or annotating the digital medical images;
   after associating the context-adaptive button with the first function, determine a second context of the digital medical images; in response to determining the second context, associate the context-adaptive button with a second function for manipulating, editing, or annotating the digital medical images;
   after associating the context-adaptive button with the second function, determine a user examination of a section of one image of the digital medical images;
   in response to determining the user examination of the section of one image of the digital medical images, associate the context-adaptive button with a third function for manipulating, editing, or annotating the digital medical images, wherein the second function is different than the third function; and receive a toggle command from the display to switch between a first toggle function for manipulating, editing, or annotating the digital medical images and a second toggle function for manipulating, editing, or annotating the digital medical images, wherein the first toggle function and the second toggle function are different.

16. The method of claim 15, wherein the digital medical images comprise at least one of:
   a breast tomosynthesis image;
   a breast 2D mammography image;
   a breast magnetic resonance image;
   a breast ultrasound image; or
   a computed tomography image.

17. The method of claim 16, wherein the first function and the second function are different and selected from one of:
   annotating at least one of the digital medical images;
   marking at least one of the digital medical images;
   magnifying at least one of the digital medical images;
   inverting at least one of the digital medical images;
   zooming at least one of the digital medical images; or
   changing the brightness or contrast of at least one of the digital medical images.

18. The method of claim 17, wherein the user examination comprises one of:
   a window adjustment of one of the digital medical images; or
   a hover over the section of the one image of the digital medical images.

19. The method of claim 18, wherein the user examination comprises the hover over the section of one image of the digital medical images and the third function is a zoom or magnification function.

* * * * *